US011007093B2

(12) United States Patent
Beitz et al.

(10) Patent No.: US 11,007,093 B2
(45) Date of Patent: May 18, 2021

(54) INCORPORATION OF APERTURED AREA INTO AN ABSORBENT ARTICLE

(71) Applicant: Kimberly-Clark Worldwide, Inc., Neenah, WI (US)

(72) Inventors: Mark J. Beitz, Appleton, WI (US); Stacy E. Evenson, Neenah, WI (US); Andrew T. Hammond, Grand Chute, WI (US); Sarah Kleuskens, Neenah, WI (US); Patrick D. Abney, Menasha, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 16/497,626

(22) PCT Filed: Mar. 30, 2017

(86) PCT No.: PCT/US2017/024911
§ 371 (c)(1),
(2) Date: Sep. 25, 2019

(87) PCT Pub. No.: WO2018/182601
PCT Pub. Date: Oct. 4, 2018

(65) Prior Publication Data
US 2020/0030161 A1 Jan. 30, 2020

(51) Int. Cl.
*A61F 13/511* (2006.01)
(52) U.S. Cl.
CPC .... *A61F 13/5116* (2013.01); *A61F 13/51104* (2013.01); *A61F 2013/51182* (2013.01)
(58) Field of Classification Search
CPC .............. A61F 13/511; A61F 13/51104; A61F 2013/51156; A61F 13/5116;
(Continued)

(56) References Cited

U.S. PATENT DOCUMENTS 2,862,251 A 12/1958 Kalwaites
3,081,515 A 3/1963 Griswold et al.
(Continued)

FOREIGN PATENT DOCUMENTS

CN 1049388 A 2/1991
CN 1299258 A 6/2001
(Continued)

OTHER PUBLICATIONS

Beaumont, Donald F. and Dr. Kenneth R. Randall, "Rotary Hydraulic Entanglement of Nonwovens," Nonwovens World, vol. 1, No. 3, Nov. 1986, pp. 76-80, reprinted from Insight 86 International Advanced Forming/Bonding Conference.
(Continued)

*Primary Examiner* — Michele M Kidwell
(74) *Attorney, Agent, or Firm* — Kimberly-Clark Worldwide

(57) ABSTRACT

An absorbent article having improved handling of body exudates. The absorbent article can minimize the amount of body exudates in contact with a wearer's skin and can minimize the incidence of leakage of body exudates from the absorbent article. The benefits of the absorbent article are achieved, in part, by a body facing material having features that help minimize contact of body exudates with the wearer's skin while also being constructed so that the body facing material does not stick to the wearer's skin in use. The body facing material includes a plurality of hollow projections, a plurality of apertures and bonded areas. The bonded areas may be formed with adhesive or by mechanical bonds.

20 Claims, 11 Drawing Sheets

(58) Field of Classification Search
CPC ........ A61F 2013/51182; A61F 13/5123; A61F
13/5125; A61F 13/51305
See application file for complete search history.

(56) References Cited

U.S. PATENT DOCUMENTS

| | | | |
|---|---|---|---|
| 3,485,706 A | 12/1969 | Evans | |
| 3,717,532 A | 2/1973 | Kamp | |
| 3,766,922 A | 10/1973 | Krusko | |
| 3,855,046 A | 12/1974 | Hansen et al. | |
| 3,917,785 A | 11/1975 | Kalwaites | |
| 4,041,951 A | 8/1977 | Sanford | |
| 4,202,868 A | 5/1980 | Hayashi et al. | |
| 4,333,979 A | 6/1982 | Sciaraffa et al. | |
| 4,614,679 A | 9/1986 | Farrington et al. | |
| 4,673,402 A | 6/1987 | Weisman et al. | |
| 4,704,112 A | 11/1987 | Suzuki et al. | |
| 4,718,152 A | 1/1988 | Suzuki et al. | |
| 4,741,941 A | 5/1988 | Englebert et al. | |
| 4,780,352 A | 10/1988 | Palumbo | |
| 4,781,710 A | 11/1988 | Megison et al. | |
| 4,805,275 A | 2/1989 | Suzuki et al. | |
| 4,868,958 A | 9/1989 | Suzuki et al. | |
| 4,879,170 A | 11/1989 | Radwanski et al. | |
| 4,931,355 A | 6/1990 | Radwanski et al. | |
| 4,939,016 A | 7/1990 | Radwanski et al. | |
| 4,950,531 A | 8/1990 | Radwanski et al. | |
| 4,970,104 A | 11/1990 | Radwanski | |
| 5,019,062 A | 5/1991 | Ryan et al. | |
| 5,137,600 A | 8/1992 | Barnes et al. | |
| 5,144,729 A | 9/1992 | Austin et al. | |
| 5,180,620 A | 1/1993 | Mende | |
| 5,242,632 A | 9/1993 | Mende | |
| 5,244,711 A | 9/1993 | Drelich et al. | |
| 5,301,401 A | 4/1994 | Suzuki et al. | |
| 5,369,858 A | 12/1994 | Gilmore et al. | |
| 5,389,202 A | 2/1995 | Everhart et al. | |
| 5,407,439 A | 4/1995 | Goulait | |
| 5,415,640 A * | 5/1995 | Kirby | A61F 13/512 604/383 |
| 5,500,270 A | 3/1996 | Langdon et al. | |
| 5,505,720 A | 4/1996 | Walters et al. | |
| 5,527,300 A | 6/1996 | Sauer | |
| 5,575,874 A | 11/1996 | Griesbach et al. | |
| 5,614,281 A | 3/1997 | Jackson et al. | |
| 5,624,427 A | 4/1997 | Bergman et al. | |
| 5,656,232 A | 8/1997 | Takai et al. | |
| 5,785,697 A | 7/1998 | Trombetta et al. | |
| 5,785,698 A | 7/1998 | Van Iten | |
| 5,830,202 A | 11/1998 | Bogdanski et al. | |
| 5,858,515 A | 1/1999 | Stokes et al. | |
| 5,888,607 A | 3/1999 | Seth et al. | |
| 5,906,879 A | 5/1999 | Huntoon et al. | |
| 5,928,212 A | 7/1999 | Kline et al. | |
| 5,962,112 A | 10/1999 | Haynes et al. | |
| 5,990,377 A | 11/1999 | Chen et al. | |
| 5,997,981 A | 12/1999 | McCormack et al. | |
| 6,022,818 A | 2/2000 | Welchel et al. | |
| 6,176,954 B1 | 1/2001 | Tsuji et al. | |
| 6,192,556 B1 | 2/2001 | Kikko et al. | |
| 6,222,092 B1 | 4/2001 | Hansen et al. | |
| 6,228,216 B1 | 5/2001 | Lindsay et al. | |
| 6,241,714 B1 | 6/2001 | Raidel et al. | |
| 6,242,074 B1 | 6/2001 | Thomas | |
| 6,290,685 B1 | 9/2001 | Insley et al. | |
| 6,290,979 B1 | 9/2001 | Roe et al. | |
| 6,291,050 B1 | 9/2001 | Cree et al. | |
| 6,314,627 B1 | 11/2001 | Ngai | |
| 6,316,687 B1 | 11/2001 | Davis et al. | |
| 6,319,455 B1 | 11/2001 | Kauschke et al. | |
| 6,331,268 B1 | 12/2001 | Kauschke et al. | |
| 6,331,345 B1 | 12/2001 | Kauschke et al. | |
| 6,395,957 B1 | 5/2002 | Chen et al. | |
| 6,413,344 B2 | 7/2002 | Bodaghi | |
| 6,417,427 B1 | 7/2002 | Roxendal et al. | |
| 6,436,512 B1 | 8/2002 | Kauschke et al. | |
| 6,440,114 B1 | 8/2002 | Bast et al. | |
| 6,468,626 B1 | 10/2002 | Takai et al. | |
| 6,488,801 B1 | 12/2002 | Bodaghi et al. | |
| 6,502,288 B2 | 1/2003 | Black et al. | |
| 6,521,555 B1 | 2/2003 | Bodaghi et al. | |
| 6,610,173 B1 | 8/2003 | Lindsay et al. | |
| 6,610,904 B1 | 8/2003 | Thomas et al. | |
| 6,660,362 B1 | 12/2003 | Lindsay et al. | |
| 6,689,242 B2 | 2/2004 | Bodaghi | |
| 6,725,512 B2 | 4/2004 | Carter | |
| 6,733,610 B2 | 5/2004 | Mizutani et al. | |
| 6,735,832 B1 | 5/2004 | Putnam et al. | |
| 6,802,932 B2 | 10/2004 | Kudo et al. | |
| 6,822,134 B1 | 11/2004 | Stiehl et al. | |
| 6,838,591 B2 | 1/2005 | Waksmundzki et al. | |
| 6,888,046 B2 | 5/2005 | Toyoshima et al. | |
| 6,911,573 B2 | 6/2005 | Chen et al. | |
| 6,911,574 B1 | 6/2005 | Mizutani | |
| 6,936,038 B2 | 8/2005 | Tears et al. | |
| 6,936,333 B2 | 8/2005 | Shizuno et al. | |
| 6,955,847 B1 | 10/2005 | Itou et al. | |
| 6,998,017 B2 | 2/2006 | Lindsay et al. | |
| 7,105,716 B2 | 9/2006 | Baratian et al. | |
| 7,132,585 B2 | 11/2006 | Kudo et al. | |
| 7,172,801 B2 | 2/2007 | Hoying et al. | |
| 7,175,613 B2 | 2/2007 | Sugiyama et al. | |
| 7,194,788 B2 | 3/2007 | Clark et al. | |
| 7,267,860 B2 | 9/2007 | Toyoshima et al. | |
| 7,294,387 B2 | 11/2007 | Wildeman | |
| 7,303,805 B2 | 12/2007 | Seth et al. | |
| 7,303,808 B2 | 12/2007 | Taneichi et al. | |
| 7,410,683 B2 | 8/2008 | Curro et al. | |
| 7,455,800 B2 | 11/2008 | Ferencz et al. | |
| 7,468,114 B2 | 12/2008 | Sato et al. | |
| 7,507,463 B2 | 3/2009 | Noda et al. | |
| 7,518,032 B2 | 4/2009 | Seyler | |
| 7,534,928 B2 | 5/2009 | Sakamoto et al. | |
| 7,547,469 B2 | 6/2009 | Provost et al. | |
| 7,553,532 B2 | 6/2009 | Turner et al. | |
| 7,553,535 B2 | 6/2009 | Noda et al. | |
| 7,569,264 B2 | 8/2009 | Toyoshima et al. | |
| 7,589,251 B2 | 9/2009 | Roe | |
| 7,632,258 B2 | 12/2009 | Misek et al. | |
| 7,648,752 B2 | 1/2010 | Hoying et al. | |
| 7,662,462 B2 | 2/2010 | Noda et al. | |
| 7,678,442 B2 | 3/2010 | Casey et al. | |
| 7,682,686 B2 | 3/2010 | Curro et al. | |
| 7,686,921 B2 | 3/2010 | Hamed et al. | |
| 7,687,681 B2 | 3/2010 | Di Luccio et al. | |
| 7,717,150 B2 | 5/2010 | Manabe et al. | |
| 7,718,243 B2 | 5/2010 | Curro et al. | |
| 7,718,249 B2 | 5/2010 | Russell et al. | |
| 7,815,995 B2 | 10/2010 | Clark et al. | |
| 7,829,173 B2 | 11/2010 | Turner et al. | |
| 7,838,099 B2 | 11/2010 | Curro et al. | |
| 7,851,047 B2 | 12/2010 | Sato et al. | |
| 7,855,314 B2 | 12/2010 | Hanao et al. | |
| 7,884,259 B2 | 2/2011 | Hanao et al. | |
| 7,897,240 B2 | 3/2011 | Noda et al. | |
| 7,935,861 B2 | 5/2011 | Suzuki | |
| 7,942,992 B2 | 5/2011 | Saka et al. | |
| 7,954,213 B2 | 6/2011 | Mizutani et al. | |
| 7,955,549 B2 | 6/2011 | Noda et al. | |
| 7,972,985 B2 | 7/2011 | Hirose et al. | |
| 7,981,822 B2 | 7/2011 | Lester, Jr. et al. | |
| 7,993,317 B2 | 8/2011 | Hammons et al. | |
| 8,022,267 B2 | 9/2011 | Hellström et al. | |
| 8,075,977 B2 | 12/2011 | Curro et al. | |
| 8,105,526 B2 | 1/2012 | Stone et al. | |
| 8,143,177 B2 | 3/2012 | Noda et al. | |
| 8,153,225 B2 | 4/2012 | Turner et al. | |
| 8,183,431 B2 | 5/2012 | Noda et al. | |
| 8,206,628 B2 | 6/2012 | Stone et al. | |
| 8,235,959 B2 | 8/2012 | Ponomarenko et al. | |
| 8,273,942 B2 | 9/2012 | Roe | |
| 8,304,600 B2 | 11/2012 | Noda et al. | |
| 8,393,374 B2 | 3/2013 | Sato et al. | |
| 8,450,557 B2 | 5/2013 | Nishitani et al. | |

(56) References Cited

U.S. PATENT DOCUMENTS

| | | | |
|---|---|---|---|
| 8,575,418 B2 | 11/2013 | Gabrielii et al. |
| 8,617,449 B2 | 12/2013 | Baker et al. |
| 8,722,173 B2 | 5/2014 | Oba et al. |
| 8,748,692 B2 | 6/2014 | Suzuki |
| 8,765,250 B2 | 7/2014 | Seyler et al. |
| 8,784,972 B2 | 7/2014 | Sato et al. |
| 8,865,965 B2 | 10/2014 | Sato et al. |
| 9,327,473 B2 | 5/2016 | Finn et al. |
| 9,445,951 B2 | 9/2016 | Moberg-Alehammar et al. |
| 9,474,660 B2 | 10/2016 | Kirby et al. |
| 9,480,608 B2 | 11/2016 | Kirby et al. |
| 9,480,609 B2 | 11/2016 | Kirby et al. |
| 9,789,009 B2 | 10/2017 | Joseph |
| 9,987,175 B2 | 6/2018 | Butler et al. |
| 10,070,999 B2 | 9/2018 | Faulks et al. |
| 10,285,874 B2 | 5/2019 | Tally et al. |
| 10,470,947 B2 | 11/2019 | Kirby et al. |
| 10,478,354 B2 | 11/2019 | Kirby et al. |
| 2001/0027302 A1 | 10/2001 | Glaug et al. |
| 2002/0034914 A1 | 3/2002 | De Leon et al. |
| 2002/0132544 A1 | 9/2002 | Takagaki |
| 2002/0143311 A1 | 10/2002 | Brisebois |
| 2003/0003832 A1 | 1/2003 | Childs et al. |
| 2003/0008108 A1 | 1/2003 | Shizuno et al. |
| 2003/0119410 A1 | 6/2003 | Bodaghi |
| 2003/0162460 A1 | 8/2003 | Saka et al. |
| 2003/0167044 A1 | 9/2003 | Toyoshima et al. |
| 2003/0181882 A1 | 9/2003 | Toyoshima et al. |
| 2003/0203162 A1 | 10/2003 | Fenwick et al. |
| 2003/0211802 A1 | 11/2003 | Keck et al. |
| 2004/0020579 A1 | 2/2004 | Durrance et al. |
| 2004/0058607 A1 | 3/2004 | Bodaghi |
| 2004/0087924 A1 | 5/2004 | Sroda et al. |
| 2004/0102124 A1 | 5/2004 | Suzuki |
| 2004/0175556 A1 | 9/2004 | Clark et al. |
| 2004/0206442 A1 | 10/2004 | Sommer et al. |
| 2005/0118389 A1 | 6/2005 | Wildeman |
| 2005/0136213 A1 | 6/2005 | Seth et al. |
| 2005/0244619 A1 | 11/2005 | Kauschke et al. |
| 2005/0261649 A1 | 11/2005 | Cohen |
| 2005/0261653 A1 | 11/2005 | Digiacomantonio et al. |
| 2005/0281976 A1 | 12/2005 | Curro et al. |
| 2006/0058772 A1 | 3/2006 | Karami |
| 2006/0069380 A1 | 3/2006 | Chen et al. |
| 2006/0122572 A1 | 6/2006 | Suarez |
| 2006/0141217 A1 | 6/2006 | Ellis et al. |
| 2006/0241558 A1 | 10/2006 | Ramshak |
| 2007/0020440 A1 | 1/2007 | Wong et al. |
| 2007/0026753 A1 | 2/2007 | Neely et al. |
| 2007/0036943 A1 | 2/2007 | Hirose et al. |
| 2007/0128411 A1 | 6/2007 | Kawai et al. |
| 2007/0130713 A1 | 6/2007 | Chen et al. |
| 2007/0172628 A1 | 7/2007 | Seth et al. |
| 2007/0255247 A1 | 11/2007 | Moberg-Alehammar et al. |
| 2008/0010795 A1 | 1/2008 | Mizutani et al. |
| 2008/0015531 A1 | 1/2008 | Hird et al. |
| 2008/0085399 A1 | 4/2008 | Noda et al. |
| 2008/0108962 A1 | 5/2008 | Furuta et al. |
| 2008/0132865 A1 | 6/2008 | Li et al. |
| 2008/0172018 A1 | 7/2008 | Chien |
| 2008/0256768 A1 | 10/2008 | Lampila et al. |
| 2008/0275415 A1 | 11/2008 | Wheeler et al. |
| 2008/0294138 A1 | 11/2008 | Andersson et al. |
| 2008/0300562 A1 | 12/2008 | Ahoniemi et al. |
| 2009/0005752 A1 | 1/2009 | Suzuki et al. |
| 2009/0030391 A1 | 1/2009 | Hammons et al. |
| 2009/0221979 A1 | 9/2009 | Huang et al. |
| 2009/0247977 A1 | 10/2009 | Takeuchi et al. |
| 2009/0264851 A1 | 10/2009 | Richlen et al. |
| 2010/0108554 A1 | 5/2010 | Melius et al. |
| 2010/0209664 A1 | 8/2010 | Sato et al. |
| 2010/0249740 A1 | 9/2010 | Miyamoto et al. |
| 2010/0274208 A1 | 10/2010 | Gabrielii et al. |
| 2010/0312211 A1 | 12/2010 | Bond et al. |
| 2011/0042011 A1 | 2/2011 | Sato et al. |
| 2011/0151196 A1 | 6/2011 | Schmidt et al. |
| 2011/0250816 A1 | 10/2011 | Fujiwara et al. |
| 2012/0059343 A1 | 3/2012 | Kume et al. |
| 2012/0111483 A1 | 5/2012 | Schneider et al. |
| 2012/0141742 A1 | 6/2012 | Yamaguchi et al. |
| 2012/0171408 A1 | 7/2012 | Turner et al. |
| 2012/0177886 A1 | 7/2012 | Kanya et al. |
| 2012/0179125 A1 | 7/2012 | Kanya et al. |
| 2012/0179126 A1 | 7/2012 | Kanya et al. |
| 2012/0189814 A1 | 7/2012 | Coslett et al. |
| 2012/0226250 A1 | 9/2012 | Sato et al. |
| 2012/0282436 A1 | 11/2012 | Coe et al. |
| 2012/0310197 A1 | 12/2012 | Thomas |
| 2012/0330260 A1 | 12/2012 | Bishop et al. |
| 2013/0034686 A1 | 2/2013 | Mitsuno |
| 2013/0178811 A1 | 7/2013 | Kikuchi et al. |
| 2013/0178815 A1 | 7/2013 | Ohashi et al. |
| 2013/0211358 A1 | 8/2013 | Kikkawa et al. |
| 2013/0304009 A1 | 11/2013 | Wang et al. |
| 2014/0005622 A1 | 1/2014 | Wirtz et al. |
| 2014/0021626 A1 | 1/2014 | Takano et al. |
| 2014/0121623 A1 | 5/2014 | Kirby et al. |
| 2014/0121624 A1* | 5/2014 | Kirby .................. A61F 13/537 604/383 |
| 2014/0121625 A1 | 5/2014 | Kirby et al. |
| 2014/0154459 A1 | 6/2014 | Krautkramer et al. |
| 2014/0234575 A1 | 8/2014 | Mitsuno et al. |
| 2015/0038933 A1 | 2/2015 | Day et al. |
| 2015/0282997 A1 | 10/2015 | Arizti et al. |
| 2015/0282998 A1 | 10/2015 | Arizti et al. |
| 2016/0039109 A1 | 2/2016 | Cecchetto et al. |
| 2016/0074256 A1 | 3/2016 | Strube et al. |
| 2016/0136011 A1 | 5/2016 | Peri et al. |
| 2016/0213520 A1 | 7/2016 | Li et al. |
| 2017/0119596 A1 | 5/2017 | Bewick-Sonntag et al. |
| 2017/0203542 A1 | 7/2017 | Ramaratnam et al. |
| 2017/0258649 A1 | 9/2017 | Rosati et al. |
| 2017/0259524 A1 | 9/2017 | Neton et al. |
| 2017/0312148 A1 | 11/2017 | Dobrosielska-Oura et al. |
| 2017/0319404 A1 | 11/2017 | Bewick-Sonntag et al. |
| 2018/0228669 A1 | 8/2018 | Schneider et al. |
| 2020/0038261 A1* | 2/2020 | Kirby ................. A61F 13/5116 |
| 2020/0337910 A1 | 10/2020 | Xu et al. |

FOREIGN PATENT DOCUMENTS

| | | |
|---|---|---|
| CN | 1348026 A | 5/2002 |
| CN | 1735394 A | 2/2006 |
| CN | 1937983 A | 3/2007 |
| CN | 101522974 A | 9/2009 |
| CN | 102264970 A | 11/2011 |
| CN | 105188630 A | 12/2015 |
| EM | 000648472 S | 6/2009 |
| EP | 0341993 A1 | 11/1989 |
| EP | 0418954 A2 | 3/1991 |
| EP | 0432882 A2 | 6/1991 |
| EP | 0446432 B1 | 8/1996 |
| EP | 0687169 B1 | 11/1999 |
| EP | 1190690 A2 | 3/2002 |
| EP | 1209271 A1 | 5/2002 |
| EP | 0863734 B1 | 6/2002 |
| EP | 1059908 B1 | 10/2004 |
| EP | 1207829 B1 | 8/2006 |
| EP | 2157223 A1 | 2/2010 |
| EP | 1902168 B1 | 7/2010 |
| EP | 1803429 B1 | 12/2011 |
| EP | 2159043 B1 | 6/2012 |
| EP | 2505173 A1 | 10/2012 |
| GB | 1088376 A | 10/1967 |
| GB | 1395402 A | 5/1975 |
| JP | 08109564 A | 4/1996 |
| JP | 2000023715 A | 1/2000 |
| JP | 3181195 B2 | 7/2001 |
| JP | 2002173863 A | 6/2002 |
| JP | 2002287228 A2 | 10/2002 |
| JP | 1172567 S | 5/2003 |
| JP | 3408078 B2 | 5/2003 |
| JP | 3453031 B2 | 10/2003 |
| JP | 2004113489 A | 4/2004 |

(56) References Cited

FOREIGN PATENT DOCUMENTS

| | | |
|---|---|---|
| JP | 2004121701 A | 4/2004 |
| JP | 1220443 S | 10/2004 |
| JP | 2005312547 A | 11/2005 |
| JP | 2005334374 A | 12/2005 |
| JP | 2007190315 A | 8/2007 |
| JP | 3989476 B2 | 10/2007 |
| JP | 3989477 B2 | 10/2007 |
| JP | 2008148807 A | 7/2008 |
| JP | 2008161302 A | 7/2008 |
| JP | 2008161319 A | 7/2008 |
| JP | 2009050621 A | 3/2009 |
| JP | 4301999 B2 | 7/2009 |
| JP | 2009153556 A | 7/2009 |
| JP | 2010024573 A | 2/2010 |
| JP | 2010115352 A | 5/2010 |
| JP | 2010133071 A | 6/2010 |
| JP | 4566109 B2 | 10/2010 |
| JP | 4627014 B2 | 2/2011 |
| JP | 2011110317 A | 6/2011 |
| JP | 4889273 B2 | 3/2012 |
| JP | 5074301 B2 | 11/2012 |
| JP | 5086035 B2 | 11/2012 |
| JP | 5087419 B2 | 12/2012 |
| JP | 1479504 S | 9/2013 |
| KR | 20100040729 A | 4/2010 |
| WO | 1990004066 A2 | 4/1990 |
| WO | 1991011161 A1 | 8/1991 |
| WO | 1998052458 A1 | 11/1998 |
| WO | 1999055532 A1 | 11/1999 |
| WO | 2001072251 A1 | 10/2001 |
| WO | 04062528 A2 | 7/2004 |
| WO | 2004059061 A1 | 7/2004 |
| WO | 2005007952 A2 | 1/2005 |
| WO | 2005007962 A1 | 1/2005 |
| WO | 2005065606 A1 | 7/2005 |
| WO | 2006007307 A1 | 1/2006 |
| WO | 2006007340 A1 | 1/2006 |
| WO | 2006011724 A1 | 2/2006 |
| WO | 2009/101591 * 8/2009 ........... A61F 13/513 |
| WO | 2010074205 A1 | 7/2010 |
| WO | 2012024576 A1 | 2/2012 |
| WO | 2013047890 A1 | 4/2013 |
| WO | 2013099624 A1 | 7/2013 |
| WO | 2014204016 A1 | 12/2014 |

OTHER PUBLICATIONS

Lemere, Mark, "Nonwoven Bonding Technologies", p. 7, Image, Inda.org, http://www.inda.org/BIO/cab2012_444_PPT.pdf.
Newbusi, "Application of non-woven fabrics on diapers and their technical development trends", Industry News, Apr. 18, 2019.
Huddersfield Textiles, "Nonwoven Manufacturing", www.tikp.co.uk/knowledge/technology/nonwovens/under-construction/?print=true, Jul. 10, 2019.
Co-pending U.S. Appl. No. 16/487,185, filed Aug. 20, 2019, by Beitz et al. for "Process for Making Fluid-Entangled Laminate Webs with Hollow Projections and Apertures".
Co-pending U.S. Appl. No. 16/597,282, filed Oct. 9, 2019, by Hammond et al. for "Absorbent Article".

* cited by examiner

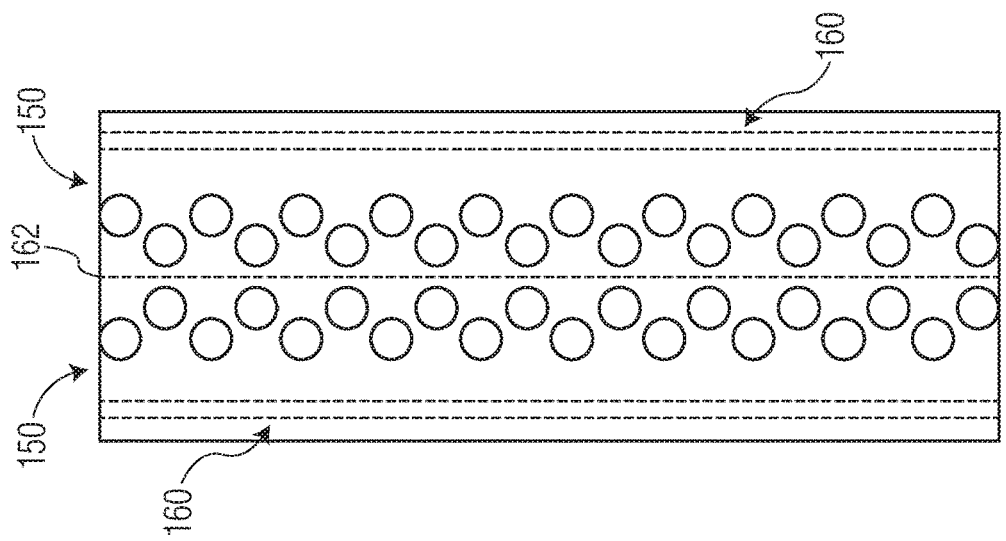
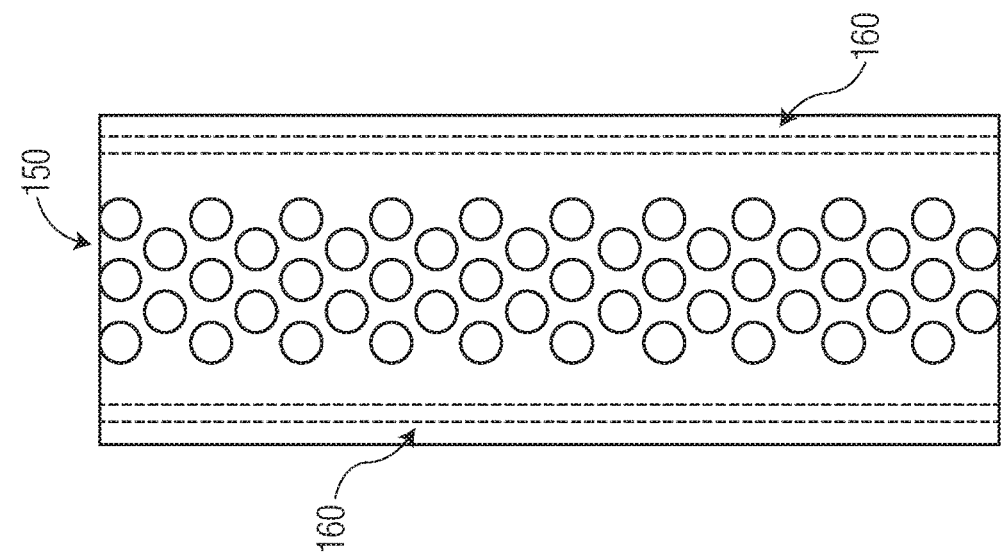
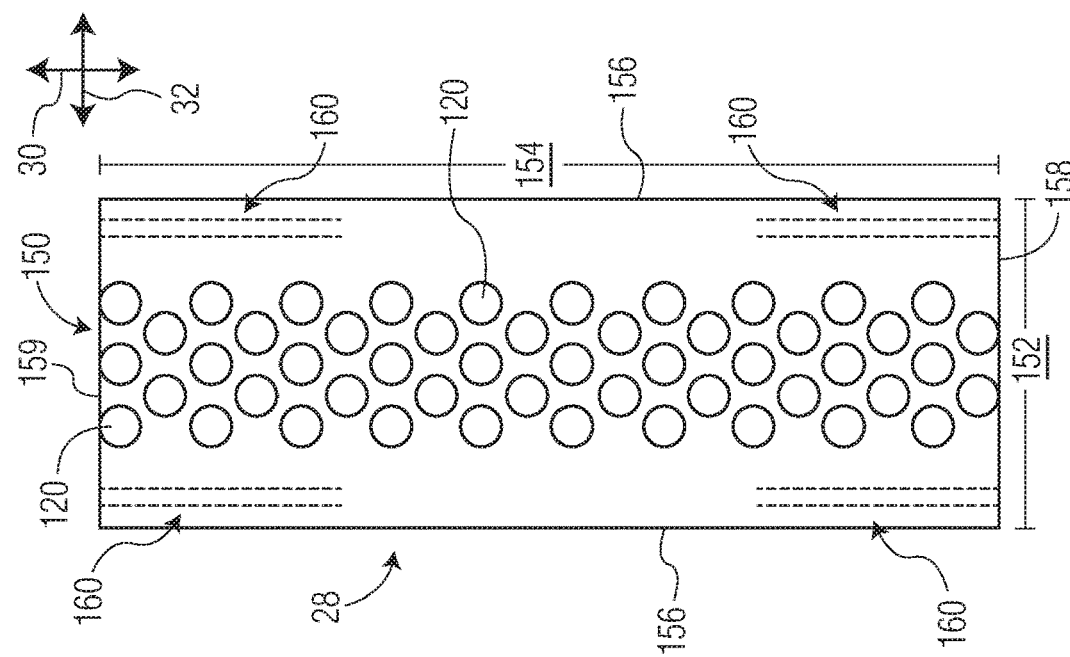

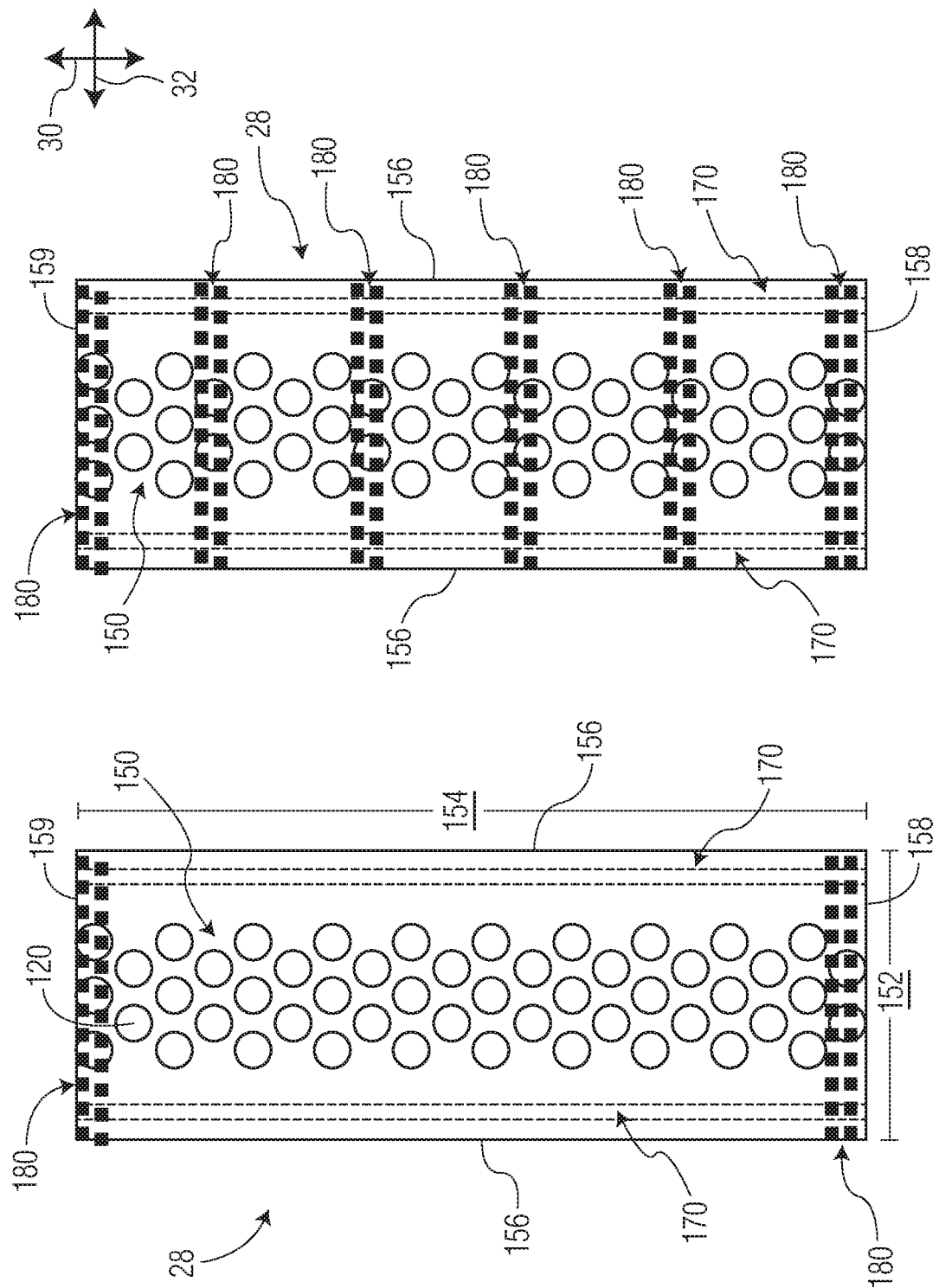

INCORPORATION OF APERTURED AREA INTO AN ABSORBENT ARTICLE

BACKGROUND

A primary function of personal care absorbent articles is to absorb and retain body exudates such as urine, fecal material, blood, and menses with additional desired attributes including low leakage of the exudates from the absorbent article and a dry feel to the wearer of the absorbent article. To accomplish these tasks, personal care absorbent articles generally have an absorbent core and a cover enclosing the absorbent core. The cover is usually fluid pervious on the body facing side of the absorbent core and fluid impervious on the garment facing side of the absorbent core. Absorbent articles commonly fail, however, to prevent leakage of body exudates. Some body exudates, such as solid and semi-solid fecal material and menses, have difficulty penetrating the body facing material of the absorbent article as easily as low viscosity exudates, such as urine, and tend to spread across the surface of the body facing material. Such spread of body exudates can result in leakage of the body exudates from the absorbent article.

Semi-solid fecal material, such as low viscosity fecal material which can be prevalent with younger children, and menses can be especially difficult to contain in an absorbent article. These exudates can move around on the body facing material of an absorbent article under the influence of gravity, motion, and pressure by the wearer of the absorbent article. The migration of the exudates is often towards the perimeter of the absorbent article, increasing the likelihood of leakage and smears against the skin of the wearer which can make clean-up of the skin difficult.

Attempts have been made in the past to provide body facing material to an absorbent article that can solve the problems described above. One such approach has been the use of various types of embossing to create three-dimensionality in the body facing surface of the absorbent article. This approach, however, requires high basis weight material to create a structure with significant topography. Furthermore, it is inherent in the embossing process that starting thickness of the material is lost due to the fact that embossing is, by its nature, a crushing and bonding process. Additionally, to "set" the embossments in a nonwoven fabric, the densified section is typically fused to create weld points that are typically impervious to the passage of body exudates. Hence, a part of the area for body exudates to transit through the material is lost. Also, "setting" the fabric can cause the material to stiffen and become harsh to the touch.

Another approach has been to form fibrous webs on three-dimensional forming surfaces. The resulting structures typically have little resilience at low basis weights (assuming soft fibers with desirable aesthetic attributes are used) and the topography is significantly degraded when wound on a roll and put through subsequent converting processes. This is partly addressed in the three-dimensional forming process by allowing the three-dimensional shape to fill with fiber. This, however, typically comes at a higher cost due to the usage of more material. This also results in a loss of softness and the resultant material becomes aesthetically unappealing for certain applications.

Another approach has been to aperture a fibrous web. Depending on the process, this can generate a flat two-dimensional web or a web with some three-dimensionality where the displaced fiber is pushed out of the plane of the original web. Typically, the extent of the three-dimensionality is limited and, under sufficient load, the displaced fiber may be pushed back toward its original position resulting in at least partial closure of the aperture. Aperturing processes that attempt to "set" the displaced fiber outside the plane of the original web are also prone to degrading the softness of the starting web. Another problem with apertured materials is that when they are incorporated into end products such as with the use of adhesives, due to their open structure, the adhesives will often readily penetrate through the apertures in the material from its underside to its top, exposed surface, thereby creating unwanted issues such as adhesive build-up in the converting process or creating unintended bonds between layers within the finished product.

There remains a need for an absorbent article that can adequately reduce the incidence of leakage of body exudates from the absorbent article. There remains a need for an absorbent article which can provide improved handling of body exudates. There remains a need for an absorbent article that can minimize the amount of body exudates in contact with the wearer's skin. For absorbent articles using a fibrous web with apertures, there remains a need for an apertured material that can be effectively placed within the article without obscuring or interfering with the apertures. There remains a need for an absorbent article that can provide physical and emotional comfort to the wearer of the absorbent article.

SUMMARY

The present invention relates generally to absorbent articles typically used for absorbing bodily exudates (for example, incontinence garments, disposable diapers, youth pants, training pants and feminine hygiene articles). The absorbent articles have an improved design and construction over prior art articles. In particular, the absorbent articles of the invention include a body facing material constructed of a fluid-entangled material and having hollow projections, apertures and land area surrounding the projections and apertures. The body facing material is attached to other components of the absorbent article by a bonded area that is discrete from the area in which the apertures are located. This particular arrangement prevents the body facing material from adhering to the wearer's skin while not interfering with the function of the apertures to separate exudates from the wearer's skin.

In an exemplary embodiment of the invention, the absorbent article includes a longitudinal direction and a lateral direction. The absorbent article has a front waist region, a back waist region and a crotch region between the front waist region and the back waist region. The absorbent article has a fluid-entangled body facing material that includes a support layer, a projection layer, a plurality of hollow projections, a plurality of apertures and a land area. The support layer includes a plurality of fibers and has first and second surfaces that are opposed to each other. The projection layer includes a plurality of fibers and has an inner surface and an outer surface that are opposed to each other. The second surface of the support layer is in contact with the inner surface of the projection layer. In addition to being in contact with each other, fibers of at least one of the support layer and the projection layer are fluid-entangled with fibers of the other of the support layer and the projection layer. The body facing material's plurality of hollow projections are formed from a first plurality of the plurality of fibers in the projection layer. The hollow projections extend from the outer surface of the projection layer in a direction away from the support layer. The body facing material's plurality of apertures are formed through the support layer and the projection layer. The plurality of apertures define an aperture area on the body facing material. The individual hollow projections and the individual apertures are surrounded by the land area of the body facing material and, therefore, the land area surrounds the plurality of hollow projection and the plurality of apertures. In addition to the elements already described, the absorbent article also includes an outer cover, an absorbent body and a secondary liner. The absorbent body has a width in the lateral direction and a length in the longitudinal direction and is positioned between the body facing material and the outer cover. The secondary liner has a width in the lateral direction and a length in the longitudinal direction. In comparison to the absorbent body, the width of the secondary liner is greater than the width of the absorbent body and the length of the secondary liner is greater the length of the absorbent body. The body facing material is attached to the secondary liner by a bonded area that is discrete from the aperture area. For clarity, with this embodiment, the bonded area and the aperture area are not in contact with each other.

The representative embodiment described above may have additional elements and features. The body facing material may include a width in the lateral direction and a length in the longitudinal direction. The body facing material also has first and second lateral edges that are opposed to each other and that extend along the length of the body facing material in the longitudinal direction. The body facing material further has a front edge and a back edge; both the front edge and the back edge extend along the length of the body facing material (the width) in the lateral direction. The bonded area extends along at least a portion of the first and second lateral edges. The bonded area may extend along the full length of the lateral edges, too. In conjunction with these aspects of the bonded area, the aperture area may have a length in the longitudinal direction and a width in the lateral direction. The width of the aperture area is typically less than the width of the body facing material and the length of the aperture area may be equal to (the same as) the length of the body facing material. Alternatively, the length of the aperture area may be less than the length of the body facing material. Independent of the length of the aperture area, the bonded areas may extend inward-starting from the first and the second lateral edges of the body facing material and extending inward in the lateral direction. The bonded areas may extend inward up until the beginning of the aperture area. The aperture area may be singular or there may be more than one aperture area. For example, the body facing material may include two aperture areas that are separated from each other by a land area. The land area separating the aperture area and the second aperture area may be attached to the secondary liner by another bonded area. The bonded areas that attach the body facing material to the secondary liner may be formed by adhesive or by mechanical bonds, such as ultrasonic, pressure or thermal bonds.

In another representative embodiment, the aperture area of the body facing material may form a "window" in the general center or slightly offset from the center of the body facing material. With this embodiment, the bonded area generally surrounds the "window" formed by the aperture area. More specifically, the bonded areas extend inward from the first and second lateral edges of the body facing material in the lateral direction. The bonded areas also extend inward from the front and back edges of the body facing material in the longitudinal direction. Each of the bonded areas extends inward up until the aperture area begins.

In another exemplary embodiment of the invention, the absorbent article includes a longitudinal direction and a lateral direction. The absorbent article has a front waist region, a back waist region and a crotch region between the front waist region and the back waist region. The absorbent article has a fluid-entangled body facing material that includes a support layer, a projection layer, a plurality of hollow projections, a plurality of apertures and a land area. The support layer includes a plurality of fibers and has first and second surfaces that are opposed to each other. The projection layer includes a plurality of fibers and has an inner surface and an outer surface that are opposed to each other. The second surface of the support layer is in contact with the inner surface of the projection layer. In addition to being in contact with each other, fibers of at least one of the support layer and the projection layer are fluid-entangled with fibers of the other of the support layer and the projection layer. The body facing material's plurality of hollow projections are formed from a first plurality of the plurality of fibers in the projection layer. The hollow projections extend from the outer surface of the projection layer in a direction away from the support layer. The body facing material's plurality of apertures are formed through the support layer and the projection layer. The plurality of apertures define an aperture area on the body facing material. The individual hollow projections and the individual apertures are surrounded by the land area of the body facing material and, therefore, the land area surrounds the plurality of hollow projection and the plurality of apertures. In addition to the elements already described, the absorbent article also includes an outer cover, an absorbent body and a secondary liner. The absorbent body has a width in the lateral direction and a length in the longitudinal direction and is positioned between the body facing material and the outer cover. The secondary liner has a width in the lateral direction and a length in the longitudinal direction. In comparison to the absorbent body, the width of the secondary liner is greater than the width of the absorbent body and the length of the secondary liner is greater the length of the absorbent body. The body facing material is attached to the secondary liner by an adhesive bonded area that is discrete from the aperture area. The body facing material is also attached to the secondary liner by a mechanical bonded area. For clarity, with this embodiment, the adhesive bonded area and the aperture area are not in contact with each other. However, the mechanical bonded area may overlap with the aperture area.

This embodiment of the invention may include additional features and components. Accordingly, the body facing material may have a width in the lateral direction and a length in the longitudinal direction. The length of the body facing material (in the longitudinal direction) defines a first lateral edge and a second lateral edge that are opposed to each other. The width of the body facing material defines a front edge and a back edge. The front edge and the back edge extend along the length of the body facing material in the lateral direction. The adhesive bonded area extends along at least a portion of the first and second lateral edges. Therefore, there may be an adhesive bonded area along the first lateral edge and a separate adhesive bonded area along the second lateral edge. The adhesive bonded areas may extend along a portion, or a part, of the lateral edges or they may extend along the full length of the lateral edges. In a further aspect of this embodiment, the aperture area has a length in the longitudinal direction and a width in the lateral direction. Typically, the width of the aperture area is less than the width of the body facing material. The length of the aperture area may be equal to the length of the body facing material. Alternatively, the length of the aperture area may be less than the length of the body facing material.

The adhesive bonded area and the mechanical bonded area function together to attach the body facing material to the secondary liner in a way that maximizes the functionality of the plurality of hollow projections and the plurality of apertures to help separate bodily exudates from the skin of the wearer of the absorbent article. There may be one or more adhesive bonded areas and there may be one or more mechanical bonded areas. A mechanical bonded area may extend from the first lateral edge of the body facing material to the second lateral edge at the front edge of the body facing material. There may be a second mechanical bonded area that extends from the first lateral edge to the second lateral edge at the back edge of the body facing material. When there are mechanical bonded areas at the front edge and the back edge of the body facing material, there may be additional mechanical bonded areas located between the front and back mechanical bonded areas. The additional mechanical bonded areas may also extend between the lateral edges of the body facing material. In a different exemplary embodiment, there may be a mechanical bonded area that extends from the front edge of the body facing material along a centerline to the back edge of the body facing material, such that the mechanical bonded area extends along the length of the body facing material in the longitudinal direction. The mechanical bonded areas may be formed by individual or "point" pressure or ultrasonic bonds. In a different exemplary embodiment, the mechanical bonded area of the invention may be formed by one or more lines of individual mechanical bonds that transverse the width of the body facing material. With this arrangement, a line of mechanical bonds starts at the first lateral edge and ends on the second lateral edge. The lines of mechanical bonds may transverse the width of the body facing material either in a straight across or diagonal across manner. When there is more than one line, there may be a combination of straight across and diagonal across lines. The lines may intersect each other and they may or may not form a pattern.

The present invention, including the exemplary embodiments, are described in greater detail in the Detailed Description along with the Drawings.

BRIEF DESCRIPTION OF THE DRAWINGS

FIG. 10A is a top down view of an illustrative embodiment of a body facing material in which there is an aperture area extending the full length of the body facing material and in which there is a bonded area on both lateral edges of the body facing material where the bonded area does not extend the full length of the body facing material.

FIG. 10B is a top down view of an illustrative embodiment of a body facing material in which there is an aperture area extending the full length of the body facing material and in which there is a bonded area on both lateral edges of the body facing material where the bonded area extends the full length of the body facing material.

FIG. 10C is a top down view of an illustrative embodiment of a body facing material in which there are two aperture areas extending the full length of the body facing material and in which there is a bonded area on both lateral edges of the body facing material where the bonded area extends the full length of the body facing material. There is also a bonded area that extends the full length of the body facing material on the land area between the two aperture areas.

FIG. 11A is a top down view of an illustrative embodiment of a body facing material in which there is an aperture area extending the full length of the body facing material and in which there is an adhesive bonded area on both lateral edges of the body facing material where the adhesive bonded area extends the full length of the body facing material. The body facing material also includes a mechanical bonded area extending between the lateral edges at the front edge and at the back edge of the body facing material.

FIG. 11B is similar to FIG. 10A except that there are additional mechanical bonded areas located at intervals between the mechanical bonded areas at the front edge and the back edge.

DETAILED DESCRIPTION

Figure 1:
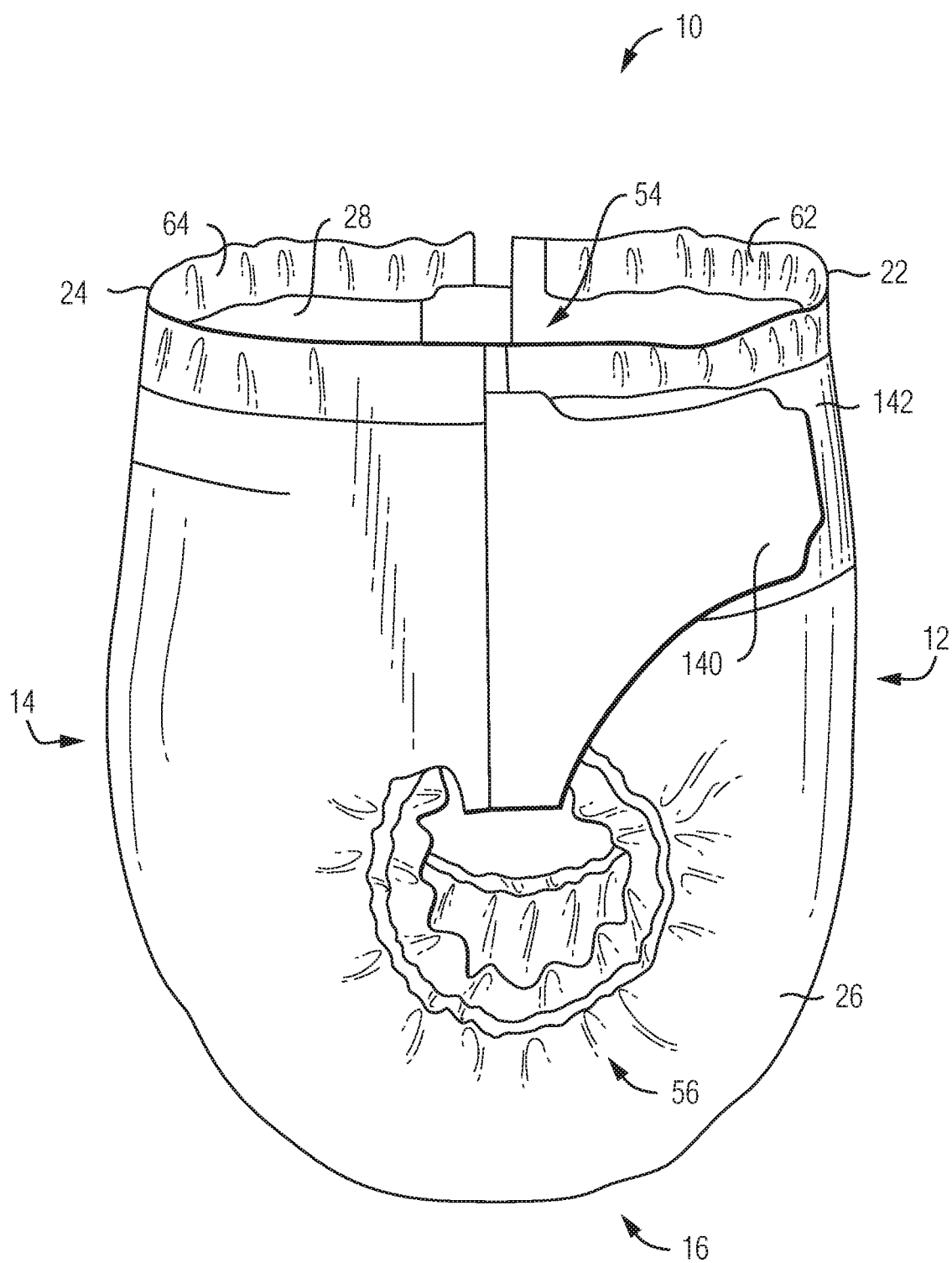
FIG. 1 is a side view illustration of an embodiment of an absorbent article.

In an embodiment, the present disclosure is generally directed towards an absorbent article which can have improved management of body exudates. In an embodiment, the present disclosure is generally directed towards an absorbent article having a body facing material which can have hollow projections extending from a surface of the body facing material. Without being bound by theory, it is believed that multiple attributes can be achieved by providing hollow projections to the body facing material. First, by providing a body facing material with hollow projections, the body facing material can have a higher degree of thickness while minimizing the amount of material used. Increased body facing material thickness can enhance the separation of the skin of the wearer from the absorbent body of an absorbent article, thereby improving the prospect of drier skin. By providing projections, land areas can be created between the projections which can temporarily distance body exudates from the high points of the projections while the body exudates can be absorbed by the absorbent article. Providing projections, therefore, can reduce skin contact with the body exudates and provide better skin benefits. Secondly, by providing projections, the spread of the body exudates on the body facing material of the absorbent article can be reduced thereby exposing less skin to contamination. Thirdly, by reducing overall skin contact, a body facing material with projections can provide a softer feel to the contacted skin thereby enhancing the tactile aesthetics of the body facing material and the absorbent article. Fourthly, when materials with projections are utilized as a body facing material for an absorbent article, the body facing material can also serve the function of acting as a cleaning aid when the absorbent article is removed from the wearer. Performance benefits are added when the body facing material includes apertures in addition to the hollow projections. The apertures provide a channel through which the body exudates may pass into the absorbent body, thereby reducing exposure of the skin to contamination. The design of the absorbent articles of the invention is optimized by providing a specific construction of the body facing material to the remainder of the article.

In order to facilitate understanding of the present invention, the following is a listing of elements and their reference numerals as they are shown in the Figures.

| Reference Numeral | Element Name |
| --- | --- |
| 10 | Disposable Absorbent Article |
| 12 | Front Waist Region |
| 14 | Back Waist Region |
| 16 | Crotch Waist Region |
| 18 | Longitudinal Side Edge |
| 20 | Longitudinal Side Edge |
| 22 | Front Waist Edge |
| 24 | Back Waist Edge |
| 26 | Outer Cover |
| 28 | Body Facing Material |
| 30 | Longitudinal Direction |
| 32 | Lateral Direction |
| 34 | Secondary Liner |
| 36 | Body Facing Surface |
| 38 | Garment Facing Surface |
| 40 | Absorbent Body |
| 42 | Longitudinal Edge of Absorbent Body |
| 44 | Longitudinal Edge of Absorbent Body |
| 46 | Front End Edge of Absorbent Body |
| 48 | Back End Edge of Absorbent Body |
| 50 | Containment Flap |
| 52 | Containment Flap |
| 54 | Central Waist Opening |
| 56 | Leg Opening |
| 58 | Flap Elastic Member |
| 60 | Flap Elastic Member |
| 62 | Front Waist Elastic Member |
| 64 | Rear Waist Elastic Member |
| 66 | Leg Elastic Member |

-continued

| Reference Numeral | Element Name |
| --- | --- |
| 68 | Leg Elastic Member |
| 70 | Outer Layer of Outer Cover |
| 72 | Inner Layer of Outer Cover |
| 74 | Wearer Facing Surface of Absorbent Body |
| 76 | Garment Facing Surface of Absorbent Body |
| 78 | Fluid Transfer Layer |
| 80 | Wearer Facing Surface of Fluid Transfer Layer |
| 82 | Garment Facing Surface of Fluid Transfer Layer |
| 84 | Acquisition Layer |
| 86 | Wearer Facing Surface of Acquisition Layer |
| 88 | Garment Facing Surface of Acquisition Layer |
| 90 | Projection in Body Facing Material |
| 92 | Support Layer of Body Facing Material |
| 94 | Projection Layer of Body Facing Material |
| 96 | First Surface of Support Layer |
| 98 | Opposed Second Surface of Support Layer |
| 100 | Thickness of Support Layer |
| 102 | Inner Surface of Projection Layer |
| 104 | Opposed Outer Surface of Projection Layer |
| 106 | Thickness of Projection Layer |
| 108 | Interface between Support and Projection Layers |
| 110 | Closed End of Projection |
| 112 | Side Wall of Projection |
| 114 | Open End of Projection |
| 116 | Land Area |
| 118 | Depression |
| 120 | Aperture |
| 122 | Side Wall Thickness of Projection |
| 124 | Interior Space of Projection |
| 126 | Migration of Fibers in First Direction |
| 128 | Migration of Fibers in Second Direction |
| 130 | Direction of Fiber Migration |
| 136 | Moveable Distal End of Containment Flap |
| 137 | Adhesive Seam |
| 138 | Fixed Proximal End of Containment Flap |
| 140 | Back Fastener |
| 142 | Front Fastener |
| 144 | Stretch Component of Back Fastener |
| 146 | Nonwoven Carrier of Back Fastener |
| 148 | Fastening Component |
| 150 | Aperture Area |
| 152 | Width of Body Facing Material |
| 154 | Length of Body Facing Material |
| 156 | Lateral Edge of Body Facing Material |
| 158 | Front Edge of Body Facing Material |
| 159 | Back Edge of Body Facing Material |
| 160 | Bonded Area |
| 162 | Additional Bonded Area |
| 170 | Adhesive Bonded Area |
| 180 | Mechanical Bonded Area |
| 190 | Line of Mechanical Bonds |

Definitions:

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, infant diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "fluid entangling" and "fluid entangled" refers herein to a formation process for further increasing the degree of fiber entanglement within a given fibrous nonwoven web or between fibrous nonwoven webs and other materials so as to make the separation of the individual fibers and/or the layers more difficult as a result of the entanglement. Generally this is accomplished by supporting the fibrous nonwoven web on some type of forming or carrier surface which has at least some degree of permeability to the impinging pressurized fluid. A pressurized fluid stream (usually multiple streams) can then be directed against the surface of the nonwoven web which is opposite the supported surface of the web. The pressurized fluid contacts the fibers and forces portions of the fibers in the direction of the fluid flow thus displacing all or a portion of a plurality of the fibers towards the supported surface of the web. The result is a further entanglement of the fibers in what can be termed the Z-direction of the web (its thickness) relative to its more planar dimension, its X-Y plane. When two or more separate webs or other layers are placed adjacent one another on the forming/carrier surface and subjected to the pressurized fluid, the generally desired result is that some of the fibers of at least one of the webs are forced into the adjacent web or layer thereby causing fiber entanglement between the interfaces of the two surfaces so as to result in the bonding or joining of the webs/layers together due to the increased entanglement of the fibers. The degree of bonding or entanglement will depend on a number of factors including, but not limited to, the types of fibers being used, the fiber lengths, the degree of pre-bonding or entanglement of the web or webs prior to subjection to the fluid entangling process, the type of fluid being used (liquids, such as water, steam or gases, such as air), the pressure of the fluid, the number of fluid streams, the speed of the process, the dwell time of the fluid and the porosity of the web or webs/other layers and the forming/carrier surface. One of the most common fluid entangling processes is referred to as hydroentangling which is a well-known process to those of ordinary skill in the art of nonwoven webs. Examples of fluid entangling process can be found in U.S. Pat. No. 4,939,016 to Radwanski et al., U.S. Pat. No. 3,485,706 to Evans, and U.S. Pat. Nos. 4,970,104 and 4,959,531 to Radwanski, each of which is incorporated herein in its entirety by reference thereto for all purposes.

The term "g/cc" refers herein to grams per cubic centimeter.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that described in U.S. Pat.

No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

Absorbent Article:

Referring to FIG. 1, a disposable absorbent article 10 of the present disclosure is exemplified in the form of a diaper. It is to be understood that the present disclosure is suitable for use with various other personal care absorbent articles, such as, for example, feminine hygiene products, without departing from the scope of the present disclosure. While the embodiments and illustrations described herein may generally apply to absorbent articles manufactured in the product longitudinal direction, which is hereinafter called the machine direction manufacturing of a product, it should be noted that one of ordinary skill could apply the information herein to absorbent articles manufactured in the latitudinal direction of the product which hereinafter is called the cross direction manufacturing of a product without departing from the spirit and scope of the disclosure. The absorbent article 10 illustrated in FIG. 1 includes a front waist region 12, a back waist region 14, and a crotch region 16 interconnecting the front and back waist regions, 12 and 14, respectively. The absorbent article 10 has a pair of longitudinal side edges, 18 and 20 (shown in FIG. 2), and a pair of opposite waist edges, respectively designated front waist edge 22 and back waist edge 24. The front waist region 12 can be contiguous with the front waist edge 22 and the back waist region 14 can be contiguous with the back waist edge 24.

Figure 2:
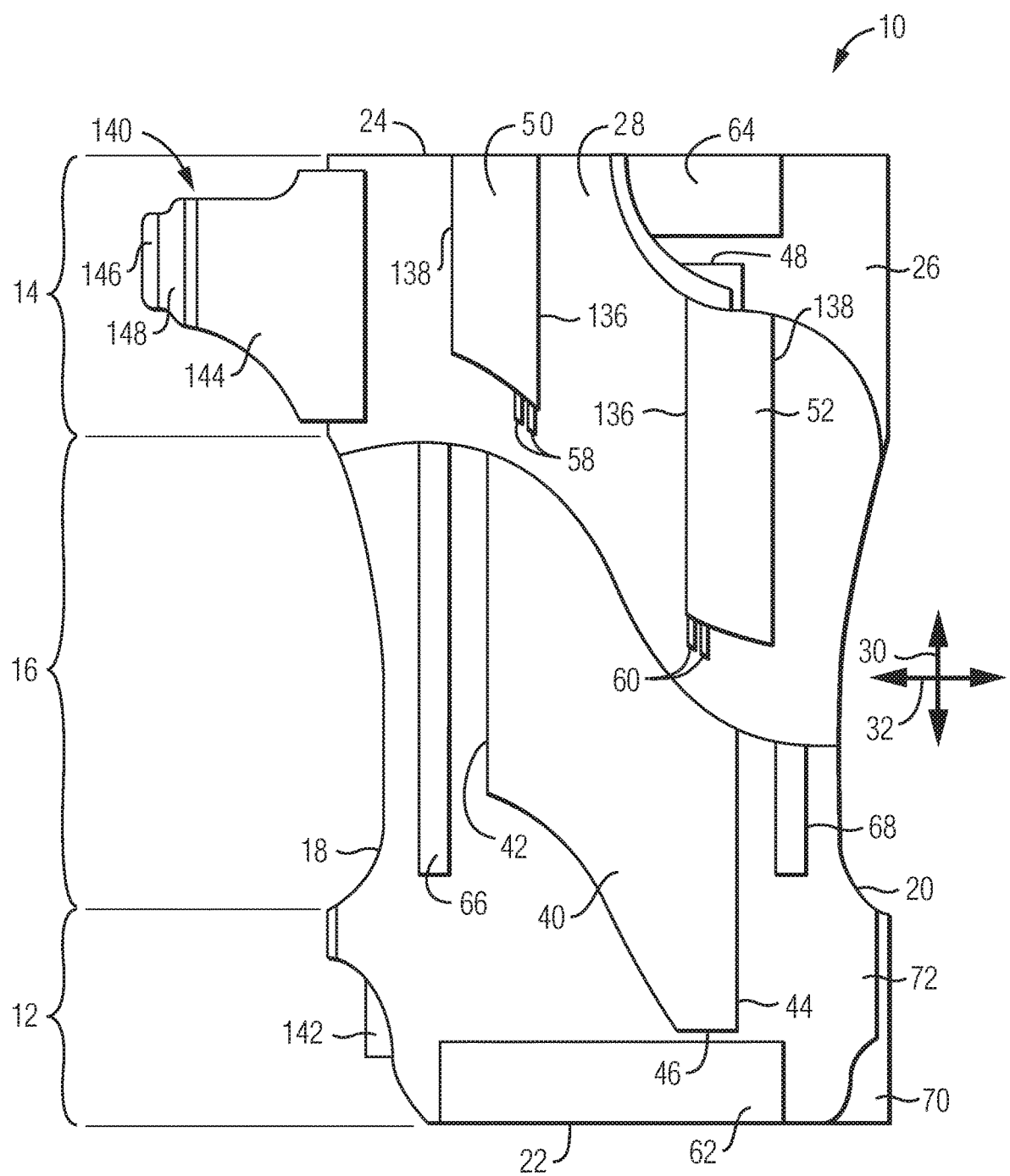
FIG. 2 is a top down view of an embodiment of an absorbent article with portions cut away for clarity.

Referring to FIG. 2, a non-limiting illustration of an absorbent article 10, such as, for example, an infant diaper, is illustrated in a top down view with portions cut away for clarity of illustration. The absorbent article 10 can include an outer cover 26 and a body facing material 28. In an embodiment, the body facing material 28 can be bonded to the outer cover 26 in a superposed relation by any suitable means such as, but not limited to, adhesives, ultrasonic bonds, thermal bonds, pressure bonds, or other conventional techniques. The outer cover 26 can define a length, or longitudinal direction 30, and a width, or lateral direction 32, which, in the illustrated embodiment, can coincide with the length and width of the absorbent article 10. The longitudinal direction 30 and the lateral direction 32 of the absorbent article 10, and of the materials which form the absorbent article 10, can provide the X-Y planes, respectively, of the absorbent article 10 and of the materials which form the absorbent article 10.

The absorbent article 10, and the materials which form the absorbent article 10, can also have a Z-direction. A measurement, taken under pressure, in the Z-direction of a material which forms the absorbent article 10 can provide a measurement of the thickness of the material. A measurement, taken under pressure, in the Z-direction of the absorbent article 10 can provide a measurement of the bulk of the absorbent article 10.

Referring to FIGS. 2-6, an absorbent body 40 can be disposed between the outer cover 26 and the body facing material 28. The absorbent body 40 can have longitudinal edges, 42 and 44, which, in an embodiment, can form portions of the longitudinal side edges, 18 and 20, respectively, of the absorbent article 10 and can have opposite end edges, 46 and 48, which, in an embodiment, can form portions of the waist edges, 22 and 24, respectively, of the absorbent article 10. In an embodiment, the absorbent body 40 can have a length and width that are the same as or less than the length and width of the absorbent article 10. In an embodiment, a pair of containment flaps, 50 and 52, can be present and can inhibit the lateral flow of body exudates.

The front waist region 12 can include the portion of the absorbent article 10 that, when worn, is positioned at least in part on the front of the wearer while the back waist region 14 can include the portion of the absorbent article 10 that, when worn, is positioned at least in part on the back of the wearer. The crotch region 16 of the absorbent article 10 can include the portion of the absorbent article 10, that, when worn, is positioned between the legs of the wearer and can partially cover the lower torso of the wearer. The waist edges, 22 and 24, of the absorbent article 10 are configured to encircle the waist of the wearer and together define the central waist opening 54 (such as shown in FIG. 1). Portions of the longitudinal side edges, 18 and 20, in the crotch region 16 can generally define leg openings 56 (such as shown in FIG. 1) when the absorbent article 10 is worn.

The absorbent article 10 can be configured to contain and/or absorb liquid, solid, and semi-solid body exudates discharged from the wearer. For example, containment flaps, 50 and 52, can be configured to provide a barrier to the lateral flow of body exudates. A flap elastic member, 58 and 60, can be operatively joined to each containment flap, 50 and 52, in any suitable manner known in the art. The elasticized containment flaps, 50 and 52, can define a partially unattached edge that can assume an upright configuration in at least the crotch region 16 of the absorbent article 10 to form a seal against the wearer's body. The containment flaps, 50 and 52, can be located along the absorbent article 10 longitudinal side edges, 18 and 20, and can extend longitudinally along the entire length of absorbent article 10 or can extend partially along the length of the absorbent article 10. Suitable construction and arrangements for containment flaps, 50 and 52, are generally well known to those skilled in the art and are described in U.S. Pat. No. 4,704,116 issued Nov. 3, 1987, to Enloe and U.S. Pat. No. 5,562,650 issued Oct. 8, 1996 to Everett et al., which are incorporated herein by reference.

Figure 4:
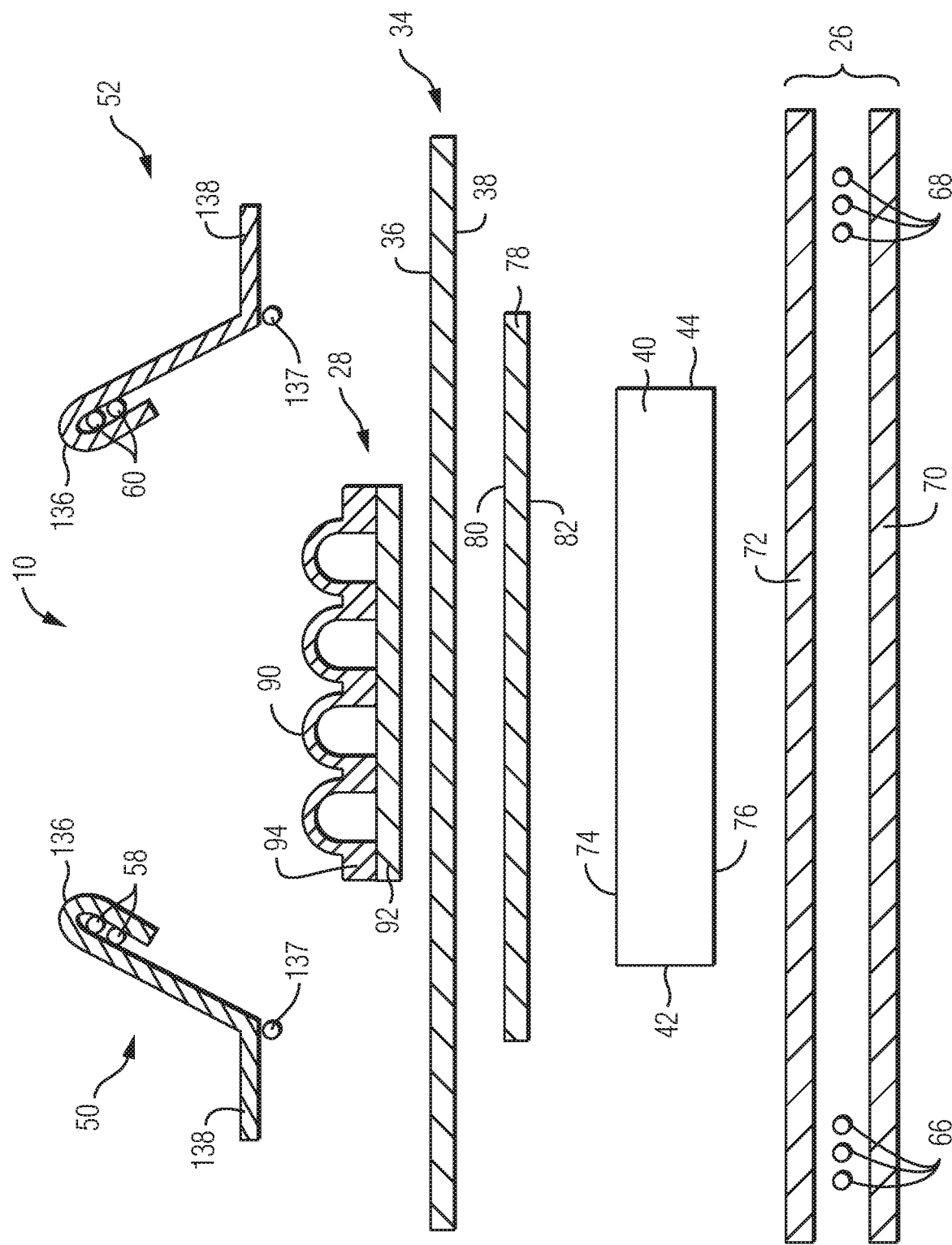
FIG. 4 is an exploded cross-sectional view of another embodiment of an absorbent article.
Figure 6:
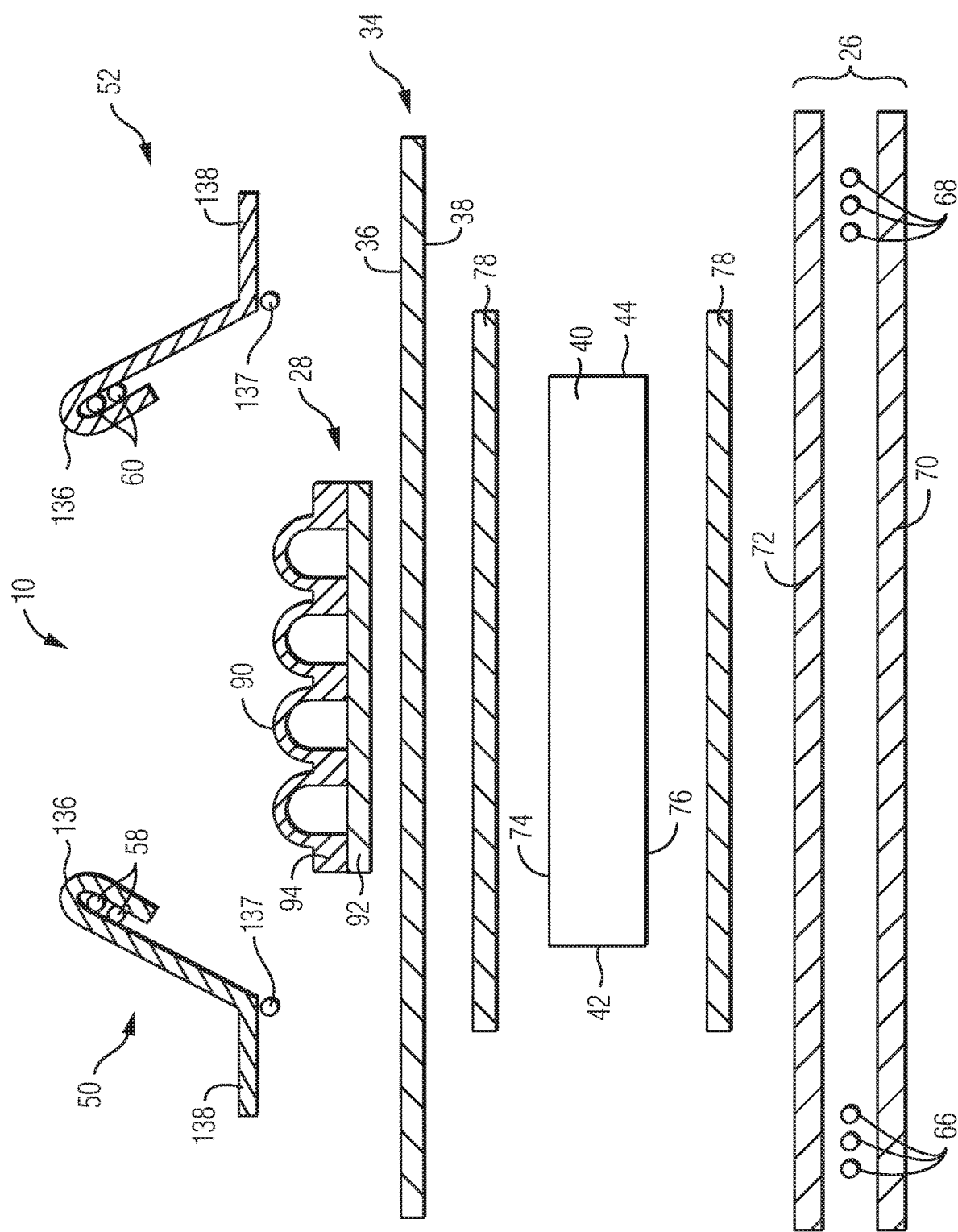
FIG. 6 is an exploded cross-sectional view of another embodiment of an absorbent article.

In various embodiments, the absorbent article 10 can include a secondary liner 34 (such as exemplified in FIG. 4 and FIG. 6). In such embodiments, the secondary liner 34 can have a body facing surface 36 and a garment facing surface 38. In such embodiments, the body facing material 28 can be bonded to the body facing surface 36 of the secondary liner 34.

To further enhance containment and/or absorption of body exudates, the absorbent article 10 can suitably include a front waist elastic member 62, a rear waist elastic member 64, and leg elastic members, 66 and 68, as are known to those skilled in the art. The waist elastic members, 62 and 64, can be attached to the outer cover 26, the body facing material 28, and/or the secondary liner 34 along the opposite waist edges, 22 and 24, and can extend over part or all of the waist edges, 22 and 24. The leg elastic members, 66 and 68, can be attached to the outer cover 26, the body facing material 28, and/or the secondary liner 34 along the opposite longitudinal side edges, 18 and 20, and positioned in the crotch region 16 of the absorbent article 10. Additional details regarding each of these elements of the absorbent article 10 described herein can be found below and with reference to the Figures.

Outer Cover:

The outer cover 26 can be breathable and/or liquid impermeable. The outer cover 26 can be elastic, stretchable or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material. In an embodiment, the outer cover 26 can be suitably stretchable, and more suitably elastic, in at least the lateral or circumferential direction 32 of the absorbent article 10. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In an embodiment such as illustrated in FIGS. 3-6, the outer cover 26 may be a two layer construction, including an outer layer 70 material and an inner layer 72 material which can be bonded together such as by a laminate adhesive. Suitable laminate adhesives can be applied continuously or intermittently as beads, a spray, parallel swirls, or the like. Suitable adhesives can be obtained from Bostik Findlay Adhesives, Inc. of Wauwatosa, Wis, U.S.A. It is to be understood that the inner layer 72 can be bonded to the outer layer 70 utilizing ultrasonic bonds, thermal bonds, pressure bonds, or the like.

The outer layer 70 of the outer cover 26 can be any suitable material and may be one that provides a generally cloth-like texture or appearance to the wearer. An example of such material can be a 100% polypropylene bonded-carded web with a diamond bond pattern available from Sandler A. G., Germany, such as 30 gsm Sawabond 4185® or equivalent. Another example of material suitable for use as an outer layer 70 of an outer cover 26 can be a 20 gsm spunbond polypropylene non-woven web. The outer layer 70 may also be constructed of the same materials from which the secondary liner 34 can be constructed as described herein.

The liquid impermeable inner layer 72 of the outer cover 26 (or the liquid impermeable outer cover 26 where the outer cover 26 is of a single-layer construction) can be either vapor permeable (i.e., "breathable") or vapor impermeable. The liquid impermeable inner layer 72 (or the liquid impermeable outer cover 26 where the outer cover 26 is of a single-layer construction) may be manufactured from a thin plastic film, although other liquid impermeable materials may also be used. The liquid impermeable inner layer 72 (or the liquid impermeable outer cover 26 where the outer cover 26 is of a single-layer construction) can inhibit liquid body exudates from leaking out of the absorbent article 10 and wetting articles, such as bed sheets and clothing, as well as the wearer and caregiver. An example of a material for a liquid impermeable inner layer 72 (or the liquid impermeable outer cover 26 where the outer cover 26 is of a single-layer construction) can be a printed 19 gsm Berry Plastics XP-8695H film or equivalent commercially available from Berry Plastics Corporation, Evansville, Ind., U.S.A.

Where the outer cover 26 is of a single layer construction, it can be embossed and/or matte finished to provide a more cloth-like texture or appearance. The outer cover 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 40 can be suitably constructed to be generally compressible, conformable, pliable, non-irritating to the wearer's skin and capable of absorbing and retaining liquid body exudates. The absorbent body 40 can be manufactured in a wide variety of sizes and shapes (for example, rectangular, trapezoidal, T-shape, I-shape, hourglass shape, etc.) and from a wide variety of materials. The size and the absorbent capacity of the absorbent body 40 should be compatible with the size of the intended wearer and the liquid loading imparted by the intended use of the absorbent article 10. Additionally, the size and the absorbent capacity of the absorbent body 40 can be varied to accommodate wearers ranging from infants to adults.

The absorbent body 40 may have a length ranging from about 150, 160, 170, 180, 190, 200, 210, 220, 225, 230, 240, 250, 260, 270, 280, 290, 300, 310, 320, 330, 340, or 350 mm to about 355, 360, 380, 385, 390, 395, 400, 410, 415, 420, 425, 440, 450, 460, 480, 500, 510, or 520 mm. The absorbent body 40 may have a crotch width ranging from about 30, 40, 50, 55, 60, 65, or 70 mm to about 75, 80, 85, 90, 95, 100, 105, 110, 115, 120, 125, 130, 140, 150, 160, 170 or 180 mm. The width of the absorbent body 40 located within the front waist region 12 and/or the back waist region 14 of the absorbent article 10 may range from about 50, 55, 60, 65, 70, 75, 80, 85, 90, or 95 mm to about 100, 105, 110, 115, 120, 125 or 130 mm. As noted herein, the absorbent body 40 can have a length and width that can be less than or equal to the length and width of the absorbent article 10.

In an embodiment, the absorbent article 10 can be a diaper having the following ranges of lengths and widths of an absorbent body 40 having an hourglass shape: the length of the absorbent body 40 may range from about 170, 180, 190, 200, 210, 220, 225, 240 or 250 mm to about 260, 280, 300, 310, 320, 330, 340, 350, 355, 360, 380, 385, or 390 mm; the width of the absorbent body 40 in the crotch region 16 may range from about 40, 50, 55, or 60 mm to about 65, 70, 75, or 80 mm; the width of the absorbent body 40 in the front waist region 12 and/or the back waist region 14 may range from about 80, 85, 90, or 95 mm to about 100, 105, or 110 mm.

In an embodiment, the absorbent article 10 may be a training pant or youth pant having the following ranges of lengths and widths of an absorbent body 40 having an hourglass shape: the length of the absorbent body 40 may range from about 400, 410, 420, 440 or 450 mm to about 460, 480, 500, 510 or 520 mm; the width of the absorbent body 40 in the crotch region 16 may range from about 50, 55, or 60 mm to about 65, 70, 75, or 80 mm; the width of the absorbent body 40 in the front waist region 12 and/or the back waist region 14 may range from about 80, 85, 90, or 95 mm to about 100, 105, 110, 115, 120, 125, or 130 mm.

In an embodiment, the absorbent article 10 can be an adult incontinence garment having the following ranges of lengths and widths of an absorbent body 40 having a rectangular shape: the length of the absorbent body 40 may range from about 400, 410 or 415 to about 425 or 450 mm; the width of the absorbent body 40 in the crotch region 16 may range from about 90, or 95 mm to about 100, 105, or 110 mm. It should be noted that the absorbent body 40 of an adult incontinence garment may or may not extend into either or both the front waist region 12 or the back waist region 14 of the absorbent article 10.

In an embodiment, the absorbent article 10 can be a feminine hygiene product having the following ranges of lengths and widths of an absorbent body 40 having an hourglass shape: the length of the absorbent body 40 may range from about 150, 160, 170, or 180 mm to about 190, 200, 210, 220, 230, 240, 250, 260, 270, 280, 290, 300, 310 or 320 mm; the width of the absorbent body in the crotch region 16 may range from about 30, 40, or 50 mm to about 60, 70, 80, 90 or 100 mm.

The absorbent body 40 can have two surfaces, 74 and 76, such as a wearer facing surface 74 and a garment facing surface 76. Edges, such as longitudinal side edges, 42 and 44, and such as front and back end edges, 46 and 48, can connect the two surfaces, 74 and 76.

In an embodiment, the absorbent body 40 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 40 can be a matrix of cellulosic fluff and superabsorbent material.

In an embodiment, the absorbent body 40 may be constructed of a single layer of materials, or in the alternative, may be constructed of two layers of materials or more. In an embodiment in which the absorbent body 40 has two layers, the absorbent body 40 can have a wearer facing layer suitably composed of hydrophilic fibers and a garment facing layer suitably composed at least in part of a high absorbency material commonly known as superabsorbent material. In such an embodiment, the wearer facing layer of the absorbent body 40 can be suitably composed of cellulosic fluff, such as wood pulp fluff, and the garment facing layer of the absorbent body 40 can be suitably composed of superabsorbent material, or a mixture of cellulosic fluff and superabsorbent material. As a result, the wearer facing layer can have a lower absorbent capacity per unit weight than the garment facing layer. The wearer facing layer may alternatively be composed of a mixture of hydrophilic fibers and superabsorbent material, as long as the concentration of superabsorbent material present in the wearer facing layer is lower than the concentration of superabsorbent material present in the garment facing layer so that the wearer facing layer can have a lower absorbent capacity per unit weight than the garment facing layer. It is also contemplated that the garment facing layer may be composed solely of superabsorbent material without departing from the scope of this disclosure. It is also contemplated that, in an embodiment, each of the layers, the wearer facing and garment facing layers, can have a superabsorbent material such that the absorbent capacities of the two superabsorbent materials can be different and can provide the absorbent body 40 with a lower absorbent capacity in the wearer facing layer than in the garment facing layer.

Various types of wettable, hydrophilic fibers can be used in the absorbent body 40. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. For example, one suitable type of fiber is a wood pulp that is a bleached, highly absorbent sulfate wood pulp containing primarily soft wood fibers. However, the wood pulp can be exchanged with other fiber materials, such as synthetic, polymeric, or meltblown fibers or with a combination of meltblown and natural fibers. In an embodiment, the cellulosic fluff can include a blend of wood pulp fluff. An example of wood pulp fluff can be "CoosAbsorb™ S Fluff Pulp" or equivalent available from Abitibi Bowater, Greenville, S.C., U.S.A., which is a bleached, highly absorbent sulfate wood pulp containing primarily southern soft wood fibers.

The absorbent body 40 can be formed with a dry-forming technique, an air-forming technique, a wet-forming technique, a foam-forming technique, or the like, as well as combinations thereof. A coform nonwoven material may also be employed. Methods and apparatus for carrying out such techniques are well known in the art.

Suitable superabsorbent materials can be selected from natural, synthetic, and modified natural polymers and materials. The superabsorbent materials can be inorganic materials, such as silica gels, or organic compounds, such as cross-linked polymers. Cross-linking may be covalent, ionic, Van der Waals, or hydrogen bonding. Typically, a superabsorbent material can be capable of absorbing at least about ten times its weight in liquid. In an embodiment, the superabsorbent material can absorb more than twenty-four times its weight in liquid. Examples of superabsorbent materials include polyacrylamides, polyvinyl alcohol, ethylene maleic anhydride copolymers, polyvinyl ethers, hydroxypropyl cellulose, carboxymal methyl cellulose, polyvinylmorpholinone, polymers and copolymers of vinyl sulfonic acid, polyacrylates, polyacrylamides, polyvinyl pyrrolidone, and the like. Additional polymers suitable for superabsorbent material include hydrolyzed, acrylonitrile grafted starch, acrylic acid grafted starch, polyacrylates and isobutylene maleic anhydride copolymers and mixtures thereof. The superabsorbent material may be in the form of discrete particles. The discrete particles can be of any desired shape, for example, spiral or semi-spiral, cubic, rod-like, polyhedral, etc. Shapes having a largest greatest dimension/smallest dimension ratio, such as needles, flakes, and fibers are also contemplated for use herein. Conglomerates of particles of superabsorbent materials may also be used in the absorbent body 40.

In an embodiment, the absorbent body 40 can be free of superabsorbent material. In an embodiment, the absorbent body 40 can have at least about 15% by weight of a superabsorbent material. In an embodiment, the absorbent body 40 can have at least about 15, 20, 25, 30, 35, 40, 45, 50, 55, 60, 65, 70, 75, 80, 85, 90, 95, 99 or 100% by weight of a superabsorbent material. In an embodiment, the absorbent body 40 can have less than about 100, 99, 95, 90, 85, 80, 75, 70, 65, 60, 55, 50, 45, 40 35, 30, 25, or 20% by weight of a superabsorbent material. In an embodiment, the absorbent body 40 can have from about 15, 20, 25, 30, 35, 40, 45, 50, 55 or 60% to about 65, 70, 75, 80, 85, 90, 95, 99 or 100% by weight of a superabsorbent material. Examples of superabsorbent material include, but are not limited to, FAVOR SXM-9300 or equivalent available from Evonik Industries, Greensboro, N.C., U.S.A. and HYSORB 8760 or equivalent available from BASF Corporation, Charlotte, N.C., U.S.A.

The absorbent body 40 can be superposed over the inner layer 72 of the outer cover 26, extending laterally between the leg elastic members, 66 and 68, and can be bonded to the inner layer 72 of the outer cover 26, such as by being bonded thereto with adhesive. However, it is to be understood that the absorbent body 40 may be in contact with, and not bonded with, the outer cover 26 and remain within the scope of this disclosure. In an embodiment, the outer cover 26 can be composed of a single layer and the absorbent body 40 can be in contact with the singer layer of the outer cover 26. In an embodiment, a layer, such as but not limited to, a fluid transfer layer 78, can be positioned between the absorbent body 40 and the outer cover 26.

Figure 3:
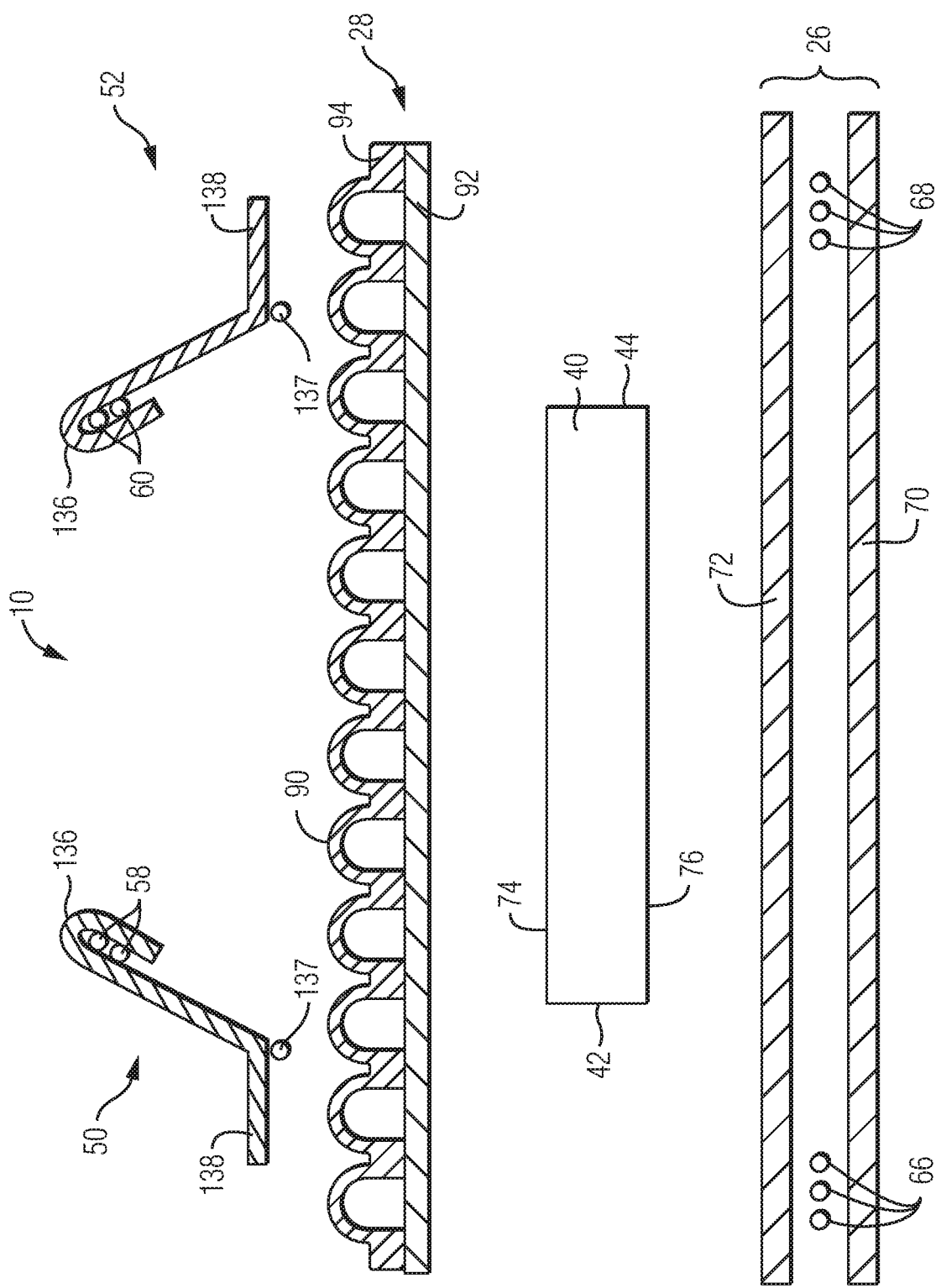
FIG. 3 is an exploded cross-sectional view of an embodiment of an absorbent article.

Fluid Transfer Layer:

In various embodiments, such as illustrated in the non-limiting example of FIG. 3, an absorbent article 10 can be constructed without a fluid transfer layer 78. In various embodiments, such as illustrated in the non-limiting examples of FIGS. 4-6, the absorbent article 10 can have a fluid transfer layer 78. The fluid transfer layer 78 can have a wearer facing surface 80 and a garment facing surface 82. In an embodiment, the fluid transfer layer 78 can be in contact with the absorbent body 40. In an embodiment, the fluid transfer layer 78 can be bonded to the absorbent body 40. Bonding of the fluid transfer layer 78 to the absorbent body 40 can occur via any means known to one of ordinary skill, such as, but not limited to, adhesives. In an embodiment, such as illustrated in the non-limiting example of FIG. 4, a fluid transfer layer 78 can be positioned between the body facing material 28 and the absorbent body 40. In an embodiment, such as illustrated in the non-limiting example of FIG. 5, a fluid transfer layer 78 can completely encompass the absorbent body 40 and can be sealed to itself. In such an embodiment, the fluid transfer layer 78 may be folded over on itself and then sealed using, for example, heat and/or pressure. In an embodiment, such as, for example, in the non-limiting illustration of FIG. 6, a fluid transfer layer 78 may be composed of separate sheets of material which can be utilized to partially or fully encompass the absorbent body 40 and which can be sealed together using a sealing means such as an ultrasonic bonder or other thermochemical bonding means or the use of an adhesive.

In an embodiment, the fluid transfer layer 78 can be in contact with and/or bonded with the wearer facing surface 74 of the absorbent body 40. In an embodiment, the fluid transfer layer 78 can be in contact with and/or bonded with the wearer facing surface 74 and at least one of the edges, 42, 44, 46 and/or 48, of the absorbent body 40. In an embodiment, the fluid transfer layer 78 can be in contact with and/or bonded with the wearer facing surface 74, at least one of the edges, 42, 44, 46 and/or 48, and the garment facing surface 76 of the absorbent body 40. In an embodiment, the absorbent body 40 may be partially or completely encompassed by a fluid transfer layer 78.

The fluid transfer layer 78 can be pliable, less hydrophilic than the absorbent body 40, and sufficiently porous to thereby permit liquid body exudates to penetrate through the fluid transfer layer 78 to reach the absorbent body 40. In an embodiment, the fluid transfer layer 78 can have sufficient structural integrity to withstand wetting thereof and of the absorbent body 40. In an embodiment, the fluid transfer layer 78 can be constructed from a single layer of material or it may be a laminate constructed from two or more layers of material.

In an embodiment, the fluid transfer layer 78 can include, but is not limited to, natural and synthetic fibers such as, but not limited to, polyester, polypropylene, acetate, nylon, polymeric materials, cellulosic materials such as wood pulp, cotton, rayon, viscose, LYOCELL® such as from Lenzing Company of Austria, or mixtures of these or other cellulosic fibers, and combinations thereof. Natural fibers can include, but are not limited to, wool, cotton, flax, hemp, and wood pulp. Wood pulps can include, but are not limited to, standard softwood fluffing grade such as "CoosAbsorb™ S Fluff Pulp" or equivalent available from Abitibi Bowater, Greenville, S.C., U.S.A., which is a bleached, highly absorbent sulfate wood pulp containing primarily southern soft wood fibers.

In various embodiments, the fluid transfer layer 78 can include cellulosic material. In various embodiments, the fluid transfer layer 78 can be creped wadding or a high-strength tissue. In various embodiments, the fluid transfer layer 78 can include polymeric material. In an embodiment, a fluid transfer layer 78 can include a spunbond material. In an embodiment, a fluid transfer layer 78 can include a meltblown material. In an embodiment, the fluid transfer layer 78 can be a laminate of a meltblown nonwoven material having fine fibers laminated to at least one spunbond nonwoven material layer having coarse fibers. In such an embodiment, the fluid transfer layer 78 can be a spunbond-meltblown ("SM") material. In an embodiment, the fluid transfer layer 78 can be a spunbond-meltblown-spunbond ("SMS") material. A non-limiting example of such a fluid transfer layer 78 can be a 10 gsm spunbond-meltblown-spunbond material. In various embodiments, the fluid transfer layer 78 can be composed of at least one material which has been hydraulically entangled into a nonwoven substrate. In various embodiments, the fluid transfer layer 78 can be composed of at least two materials which have been hydraulically entangled into a nonwoven substrate. In various embodiments, the fluid transfer layer 78 can have at least three materials which have been hydraulically entangled into a nonwoven substrate. A non-limiting example of a fluid transfer layer 78 can be a 33 gsm hydraulically entangled substrate. In such an example, the fluid transfer layer 78 can be a 33 gsm hydraulically entangled substrate composed of a 12 gsm spunbond material, a 10 gsm wood pulp material having a length from about 0.6 cm to about 5.5 cm, and an 11 gsm polyester staple fiber material. To manufacture the fluid transfer layer 78 just described, the 12 gsm spunbond material can provide a base layer while the 10 gsm wood pulp material and the 11 gsm polyester staple fiber material can be homogeneously mixed together and deposited onto the spunbond material and then hydraulically entangled with the spunbond material.

In various embodiments, a wet strength agent can be included in the fluid transfer layer 78. A non-limiting example of a wet strength agent can be Kymene 6500 (557LK) or equivalent available from Ashland Inc. of Ashland, Ky., U.S.A. In various embodiments, a surfactant can be included in the fluid transfer layer 78. In various embodiments, the fluid transfer layer 78 can be hydrophilic. In various embodiments, the fluid transfer layer 78 can be hydrophobic and can be treated in any manner known in the art to be made hydrophilic.

In an embodiment, the fluid transfer layer 78 can be in contact with and/or bonded with an absorbent body 40 which is made at least partially of particulate material such as superabsorbent material. In an embodiment in which the fluid transfer layer 78 at least partially or completely encompasses the absorbent body 40, the fluid transfer layer 78 should not unduly expand or stretch as this might cause the particulate material to escape from the absorbent body 40. In an embodiment, the fluid transfer layer 78, while in a dry state, should have respective extension values at peak load in the machine and cross directions of 30 percent or less and 40 percent or less, respectively.

In an embodiment, the fluid transfer layer 78 may have a longitudinal length the same as, greater than, or less than the longitudinal length of the absorbent body 40. The fluid transfer layer 78 can have a longitudinal length ranging from about 150, 160, 170, 180, 190, 200, 210, 220, 225, 230, 240, 250, 260, 270, 280, 290, 300, 310, 320, 330, 340, or 350 mm to about 355, 360, 380, 385, 390, 395, 400, 410, 415, 420, 425, 440, 450, 460, 480, 500, 510, or 520 mm.

Figure 5:
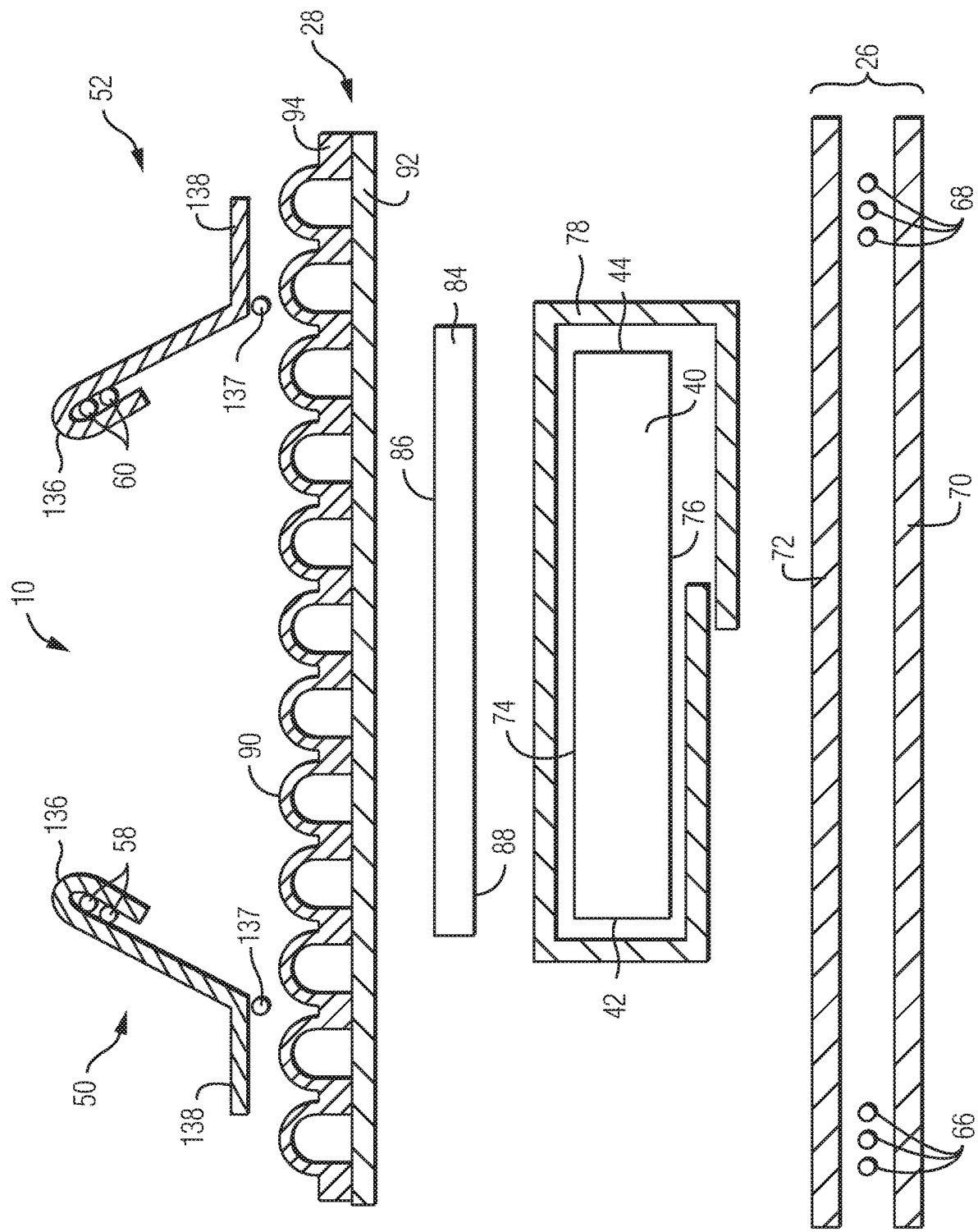
FIG. 5 is an exploded cross-sectional view of another embodiment of an absorbent article.

Acquisition Layer:

In various embodiments, such as illustrated, for example, in FIG. 5, the absorbent article 10 can have an acquisition layer 84. The acquisition layer 84 can help decelerate and diffuse surges or gushes of liquid body exudates penetrating the body facing material 28. In an embodiment, the acquisition layer 84 can be positioned between the body facing material 28 and the absorbent body 40 to take in and distribute body exudates for absorption by the absorbent body 40. In an embodiment, the acquisition layer 84 can be positioned between the body facing material 28 and a fluid transfer layer 78 if a fluid transfer layer 78 is present. In an embodiment, the acquisition layer 84 can be positioned between a secondary liner 34, if present, and the absorbent body 40.

The acquisition layer 84 can have a wearer facing surface 86 and a garment facing surface 88. In an embodiment, the acquisition layer 84 can be in contact with and/or bonded with the body facing material 28. In an embodiment in which the acquisition layer 84 is bonded with the body facing material 28, bonding of the acquisition layer 84 to the body facing material 28 can occur through the use of an adhesive and/or point fusion bonding. The point fusion bonding can be selected from, but is not limited to, ultrasonic bonding, pressure bonding, thermal bonding, and combinations thereof. In an embodiment, the point fusion bonding can be provided in any pattern as deemed suitable.

The acquisition layer 84 may have any longitudinal length dimension as deemed suitable. The acquisition layer 84 may have a longitudinal length from about 120, 130, 140, 150, 160, 170, 180, 190, 200, 210, 220, 225, 230, 240, or 250 mm to about 260, 270, 280, 290, 300, 310, 320, 340, 350, 360, 380, 400, 410, 415, 420, 425, 440, 450, 460, 480, 500, 510 or 520 mm. In an embodiment, the acquisition layer 84 can have any length such that the acquisition layer 84 can be coterminous with the waist edges, 22 and 24, of the absorbent article 10.

In an embodiment, the longitudinal length of the acquisition layer 84 can be the same as the longitudinal length of the absorbent body 40. In such an embodiment the midpoint of the longitudinal length of the acquisition layer 84 can substantially align with the midpoint of the longitudinal length of the absorbent body 40.

In an embodiment, the longitudinal length of the acquisition layer 84 can be shorter than the longitudinal length of the absorbent body 40. In such an embodiment, the acquisition layer 84 may be positioned at any desired location along the longitudinal length of the absorbent body 40. As an example of such an embodiment, the absorbent article 10 may contain a target area where repeated liquid surges typically occur in the absorbent article 10. The particular location of a target area can vary depending on the age and gender of the wearer of the absorbent article 10. For example, males tend to urinate further toward the front region of the absorbent article 10 and the target area may be phased forward within the absorbent article 10. For example, the target area for a male wearer may be positioned about 2¾" forward of the longitudinal midpoint of the absorbent body 40 and may have a length of about ±3" and a width of about ±2". The female target area can be located closer to the center of the crotch region 16 of the absorbent article 10. For example, the target area for a female wearer may be positioned about 1" forward of the longitudinal midpoint of the absorbent body 40 and may have a length of about ±3" and a width of about ±2". As a result, the relative longitudinal placement of the acquisition layer 84 within the absorbent article 10 can be selected to best correspond with the target area of either or both categories of wearers.

In an embodiment, the absorbent article 10 may contain a target area centered within the crotch region 16 of the absorbent article 10 with the premise that the absorbent article 10 would be worn by a female wearer. The acquisition layer 84, therefore, may be positioned along the longitudinal length of the absorbent article 10 such that the acquisition layer 84 can be substantially aligned with the target area of the absorbent article 10 intended for a female wearer. Alternatively, the absorbent article 10 may contain a target area positioned between the crotch region 16 and the front waist region 12 of the absorbent article 10 with the premise that the absorbent article 10 would be worn by a male wearer. The acquisition layer 84, therefore, may be positioned along the longitudinal length of the absorbent article 10 such that the acquisition layer 84 can be substantially aligned with the target area of the absorbent article 10 intended for a male wearer.

In an embodiment, the acquisition layer 84 can have a size dimension that is the same size dimension as the target area of the absorbent article 10 or a size dimension greater than the size dimension of the target area of the absorbent article 10. In an embodiment, the acquisition layer 84 can be in contact with and/or bonded with the body facing material 28 at least partially in the target area of the absorbent article 10.

In various embodiments, the acquisition layer 84 can have a longitudinal length shorter than, the same as or longer than the longitudinal length of the absorbent body 40. In an embodiment in which the absorbent article 10 is a diaper, the acquisition layer 84 may have a longitudinal length from about 120, 130, 140, 150, 160, 170, or 180 mm to about 200, 210, 220, 225, 240, 260, 280, 300, 310 or 320 mm. In such an embodiment, the acquisition layer 84 may be shorter in longitudinal length than the longitudinal length of the absorbent body 40 and may be phased from the front end edge 46 of the absorbent body 40 a distance of from about 15, 20, or 25 mm to about 30, 35 or 40 mm. In an embodiment in which the absorbent article 10 may be a training pant or youth pant, the acquisition layer 84 may have a longitudinal length from about 120, 130, 140, 150, 200, 210, 220, 230, 240 or 250 mm to about 260, 270, 280, 290, 300, 340, 360, 400, 410, 420, 440, 450, 460, 480, 500, 510 or 520 mm. In such an embodiment, the acquisition layer 84 may have a longitudinal length shorter than the longitudinal length of the absorbent body 40 and may be phased a distance of from about 25, 30, 35 or 40 mm to about 45, 50, 55, 60, 65, 70, 75, 80 or 85 mm from the front end edge 46 of the absorbent body 40. In an embodiment in which the absorbent article 10 is an adult incontinence garment, the acquisition layer 84 may have a longitudinal length from about 200, 210, 220, 230, 240, or 250 mm to about 260, 270, 280, 290, 300, 320, 340, 360, 380, 400, 410, 415, 425, or 450 mm. In such an embodiment, the acquisition layer 84 may have a longitudinal length shorter than the longitudinal length of the absorbent body 40 and the acquisition layer 84 may be phased a distance of from about 20, 25, 30 or 35 mm to about 40, 45, 50, 55, 60, 65, 70 or 75 mm from the front end edge 46 of the absorbent body 40.

The acquisition layer 84 may have any width as desired. The acquisition layer 84 may have a width dimension from about 15, 20, 25, 30, 35, 40, 45, 50, 55, 60, or 70 mm to about 80, 90, 100, 110, 115, 120, 130, 140, 150, 160, 170, or 180 mm. The width of the acquisition layer 84 may vary dependent upon the size and shape of the absorbent article 10 within which the acquisition layer 84 will be placed. The acquisition layer 84 can have a width smaller than, the same as, or larger than the width of the absorbent body 40. Within the crotch region 16 of the absorbent article 10, the acquisition layer 84 can have a width smaller than, the same as, or larger than the width of the absorbent body 40.

In an embodiment, the acquisition layer 84 can include natural fibers, synthetic fibers, superabsorbent material, woven material, nonwoven material, wet-laid fibrous webs, a substantially unbounded airlaid fibrous web, an operatively bonded, stabilized-airlaid fibrous web, or the like, as well as combinations thereof. In an embodiment, the acquisition layer 84 can be formed from a material that is substantially hydrophobic, such as a nonwoven web composed of polypropylene, polyethylene, polyester, and the like, and combinations thereof.

In various embodiments, the acquisition layer 84 can have fibers which can have a denier of greater than about 5. In various embodiments, the acquisition layer 84 can have fibers which can have a denier of less than about 5.

In an embodiment, the acquisition layer 84 can be a through-air bonded-carded web such as a 50 gsm through-air bonded-carded web composite having a homogenous blend of about 50% sheath/core bicomponent polyethylene/polypropylene fibers having a fiber diameter of 3 denier and about 50% sheath/core bicomponent polyethylene/polypropylene fibers having a fiber diameter of 1.5 denier. An example of such a composite is a composite having about 50% ES FiberVisions 3 denier ESC-233 bicomponent fibers and about 50% ES FiberVisions 1.5 denier ESC-215 bicomponent fibers, or equivalent composite, available from ES FiberVisions Corp., Duluth, Ga., U.S.A.

In an embodiment, the acquisition layer 84 can be a through-air bonded-carded web such as a 50 gsm through-air bonded-carded web composite having a homogenous blend of about 50% Rayon fibers having a fiber diameter of 3 denier and about 50% sheath/core bicomponent polyethylene/polypropylene fibers having a fiber diameter of 1.5 denier. An example of such a composite is a composite having about 50% Kelheim 3 denier Rayon Galaxy fibers and about 50% ES FiberVisions 1.5 denier ESC-215 bicomponent fibers, or equivalent composite, available from ES FiberVisions Corp., Duluth, Ga., U.S.A.

In an embodiment, the acquisition layer 84 can be a through-air bonded-carded web such as a 50 gsm through-air bonded-carded web composite having a homogenous blend of about 40% hollow polypropylene fibers having a fiber diameter of 7 denier and about 60% sheath/core bicomponent polyethylene/polypropylene fibers having a fiber diameter of 17 denier. An example of such a composite is a composite having about 40% ES FiberVisions 7 denier T-118 hollow polypropylene fibers and about 60% ES FiberVisions 17 denier Varde bicomponent fibers, or equivalent composite, available from ES FiberVisions Corp., Duluth, Ga., U.S.A.

In an embodiment, the acquisition layer 84 can be a through-air bonded-carded web such as a 35 gsm through-air bonded-carded web composite having a homogenous mixture of about 35% sheath/core bicomponent polyethylene/polypropylene fibers having a fiber diameter of 6 denier, about 35% sheath/core bicomponent polyethylene/polypropylene fibers having a fiber diameter of 2 denier, and about 30% polyester fibers having a fiber diameter of 6 denier. An example of such a composite is a composite having about 35% Huvis 180-N (PE/PP 6d), about 35% Huvis N-215 (PE/PP 2d), and about 30% Huvis SD-10PET 6d, or equivalent composite, available from SamBo Company, Ltd, Korea.

In an embodiment, the acquisition layer 84 can be a thermally bonded, stabilized-airlaid fibrous web (e.g. Concert product code DT200.100.D0001) which is available from Glatfelter, a business having offices located in York, Pa., U.S.A.

In an embodiment, the acquisition layer 84 can include a coform/foam material. In an embodiment, the acquisition layer 84 can include a resilient coform material. As used herein, the term "coform" refers to a blend of meltblown fibers and absorbent fibers such as cellulosic fibers that can be formed by air forming a meltblown polymer material while simultaneously blowing air-suspended fibers into the stream of meltblown fibers. The coform material can also include other materials, such as superabsorbent material. The meltblown fibers and absorbent fibers (and other optional materials) can be collected on a forming surface, such as provided by a foraminous belt. The forming surface can include a gas-pervious material that has been placed onto the forming surface. Coform materials are further described in U.S. Pat. Nos. 5,508,102 and 5,350,624 to Georger et al. and U.S. Pat. No. 4,100,324 to Anderson and U.S. Publication No. 2012/0053547 to Schroeder et al., which are incorporated herein in their entirety by reference thereto and to the extent they do not conflict herewith. As used herein, the term "resilient coform" refers to a resilient coform nonwoven layer including a matrix of meltblown fibers and an absorbent material, wherein the meltblown fibers constitute from about 30 wt % to about 99 wt % of the web and the absorbent material constitutes from about 1 wt % to about 70 wt % of the web, and further wherein the meltblown fibers being formed from a thermoplastic composition that contains at least one propylene/α-olefin copolymer having a propylene content of from about 60 mole % to about 99.5 mole % and an α-olefin content of from about 0.5 mole % to about 40 mole %, wherein the copolymer further has a density of from about 0.86 to about 0.90 grams per cubic centimeter and the composition has a melt flow rate of from about 120 to about 6000 grams per 10 minutes, determined at 230° C. in accordance with ASTM Test Method D1238-E, although practical considerations can reduce the high end melt flow rate range.

The acquisition layer 84 may have additional parameters including basis weight and thickness. In an embodiment, the basis weight of the acquisition layer 84 can be at least about 10 or 20 gsm. In an embodiment, the basis weight of the acquisition layer 84 can be from about 10, 20, 30, 40, 50 or 60 gsm to about 65, 70, 75, 80, 85, 90, 100, 110, 120, or 130 gsm. In an embodiment, the basis weight of the acquisition layer 84 can be less than about 130, 120, 110, 100, 90, 85, 80, 75, 70, 65, 60 or 50 gsm. In an embodiment, the acquisition layer 84 can have a thickness, measured at 0.05 psi (0.345 kPa), of less than about 1.5 mm. In an embodiment, such as, for example, when the absorbent article 10 can be a diaper, the acquisition layer 84 can have a thickness, measured at 0.05 psi (0.345 kPa), of less than about 1.5, 1.25, or 1.0 mm. In an embodiment, such as, for example, when the absorbent article can be a feminine hygiene product, the acquisition layer 84 can have a thickness, measured at 0.2 psi (1.379 kPa), of less than about 1.5, 1.25, or 1.0 mm.

Figure 7:
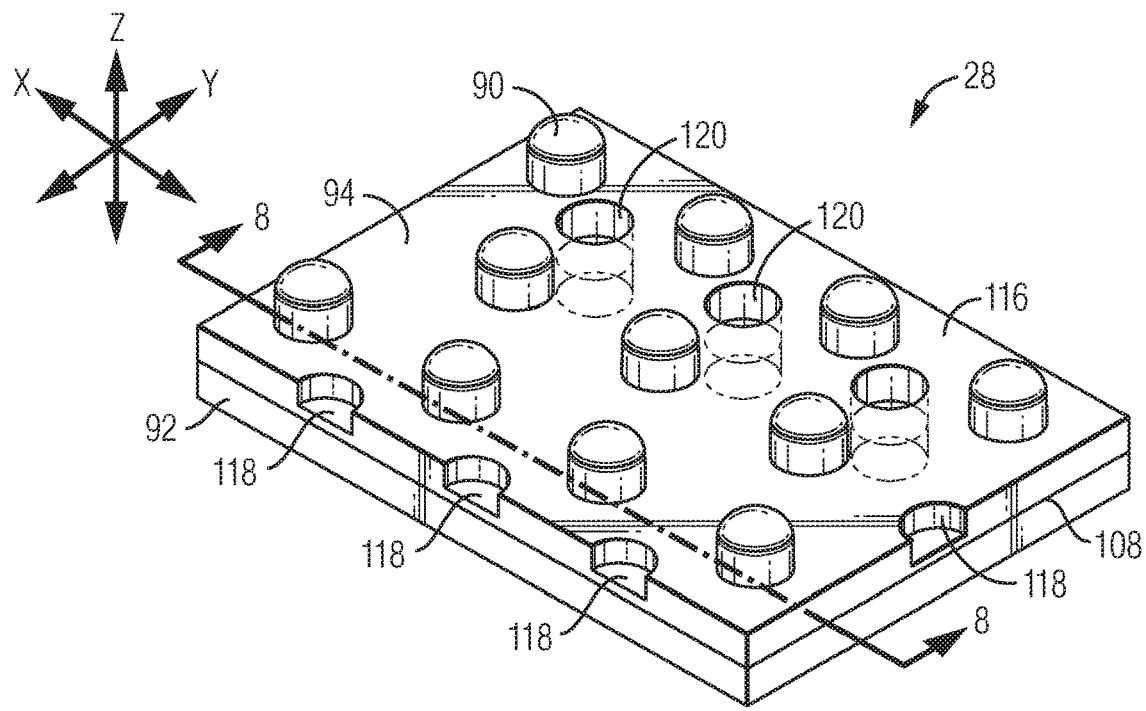
FIG. 7 is a perspective view of an embodiment of a body facing material.
Figure 8:
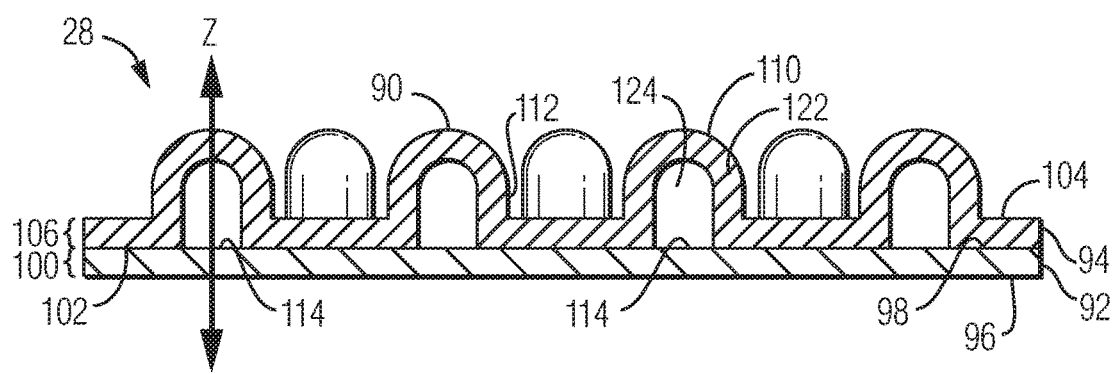
FIG. 8 is a cross-sectional view of the body facing material of FIG. 7 taken along line 8-8.
Figure 9:
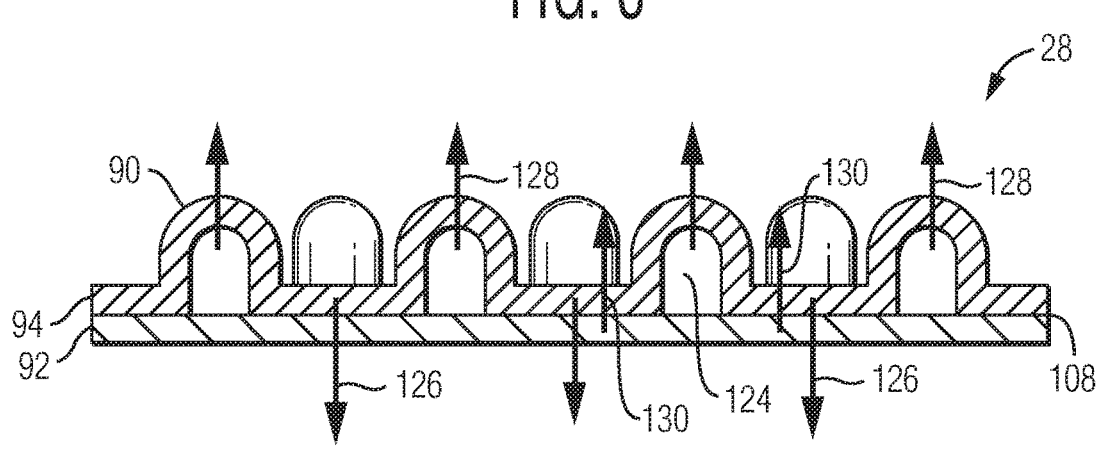
FIG. 9 is a cross-sectional view of the body facing material of FIG. 7 taken along line 8-8 of FIG. 7 showing possible directions of fiber movements within the body facing material due to a fluid entanglement process.

Body Facing Material:

As illustrated in FIGS. 7-9, a body facing material 28 can be a fluid entangled laminate web with projections 90 extending outwardly and away from at least one intended external surface of the laminate web. In an embodiment, the projections 90 can be hollow. The body facing material 28 can have two layers such as a support layer 92 and a projection layer 94. The support layer 92 can have a first surface 96 and an opposed second surface 98 as well as a thickness 100. The projection layer 94 can have an inner surface 102 and an opposed outer surface 104 as well as a thickness 106. An interface 108 can be present between the support layer 92 and the projection layer 94. In an embodiment, fibers of the projection layer 94 can cross the interface 108 and be entangled with and engage the support layer 92 so as to form the body facing material 28. In an embodiment in which the support layer 92 is a fibrous nonwoven web, the fibers of the support layer 92 may cross the interface 108 and be entangled with the fibers in the projection layer 94.

Projections of Body Facing Material

In an embodiment, the projections 90 can be filled with fibers from the projection layer 94 and/or the support layer 92. In an embodiment, the projections 90 can be hollow. The projections 90 can have closed ends 110 and side walls 112. In various embodiments, the projections 90 can have a percentage of open area in which light can pass through the projections 90 unhindered by the material forming the projections 90, such as, for example, fibrous material. The percentage of open area present in the projections 90 encompasses all area of the projection 90 where light can pass through the projection 90 unhindered. Thus, for example, the percentage of open area of a projection 90 can encompass all open area of the projection 90 via apertures, interstitial fiber-to-fiber spacing, and any other spacing within the projection 90 where light can pass through unhindered. In an embodiment, the open area can be due to the interstitial fiber-to-fiber spacing. The actual shape of the projections 90 can be varied depending on the shape of the forming surface into which the fibers from the projection layer 94 are forced. Thus, while not limiting the variations, the shapes of the projections 90 may be, for example, round, oval, square, rectangular, triangular, diamond-shaped, etc. Both the width and height of the projections 90 can be varied as can be the spacing and pattern of the projections 90. In an embodiment, various shapes, sizes and spacing of the projections 90 can be utilized in the same projection layer 94. In an embodiment, the projections 90 can have a height of greater than about 1 mm. In an embodiment, the projections 90 can have a height greater than about 1, 2, 3, 4, 5, 6, 7, 8, 9, or 10 mm. In an embodiment, the projections 90 can have a height from about 1, 2, 3, 4, or 5 mm to about 6, 7, 8, 9 or 10 mm.

The projections 90 of the body facing material 28 can be located on and emanate from the outer surface 104 of the projection layer 94. In an embodiment, the projections 90 can extend from the outer surface 104 of the projection layer 94 in a direction away from the support layer 92. In an embodiment in which the projections 90 can be hollow, they can have open ends 114 which can be located towards the inner surface 102 of the projection layer 94 and can be covered by the second surface 98 of the support layer 92 or the inner surface 102 of the projection layer 94 depending upon the amount of fiber that has been used from the projection layer 94 to form the projections 90. The projections 90 can be surrounded by land areas 116 which can be formed from the outer surface 104 of the projection layer 94 though the thickness of the land areas 116 can be comprised of both the projection layer 94 and the support layer 92. The land areas 116 can be relatively flat and planar, as shown in FIGS. 7 and 8, or topographical variability may be built into the land areas 116. For example, in an embodiment, a land area 116 may have a plurality of three-dimensional shapes formed into it by forming the projection layer 94 on a three-dimensionally-shaped forming surface such as is disclosed in U.S. Pat. No. 4,741,941 to Engelbert et al. assigned to Kimberly-Clark Worldwide and incorporated herein by reference in its entirety for all purposes. For example, in an embodiment, a land area 116 may be provided with depressions 118 which can extend all or part way into the projection layer 94 and/or the support layer 92. In addition, a land area 116 may be subjected to embossing which can impart surface texture and other functional attributes to the land area 116. In an embodiment, a land area 116 and the body facing material 28 as a whole may be provided with apertures 120 which can extend through the body facing material 28 so as to further facilitate the movement of fluids (such as the liquids and solids that make up body exudates) into and through the body facing material 28. Such apertures 120 are to be distinguished from interstitial fiber-to-fiber spacing, which is the spacing from one individual fiber to the next individual fiber.

The projections 90 of the body facing material 28 can be provided in any orientation as deemed suitable. In an embodiment, the projections 90 of the body facing material 28 can be provided randomly to the body facing material 28. In an embodiment, the projections 90 can be oriented linearly in the longitudinal direction 30 of the absorbent article 10. In an embodiment, the projections 90 can be oriented linearly in the lateral direction 32 of the absorbent article 10. In an embodiment, the projections 90 can be oriented linearly in a direction which can be at an angle to the longitudinal direction 30 and/or the lateral direction 32 of the absorbent article 10. The land areas 116 of the body facing material 28 can be provided in any orientation as deemed suitable. In an embodiment, the land areas 116 can be oriented linearly in the longitudinal direction 30 of the absorbent article 10. In an embodiment, the land areas 116 can be oriented linearly in the lateral direction 32 of the absorbent article 10. In an embodiment, the land areas 116 can be oriented linearly in a direction which can be at an angle to the longitudinal direction 30 and/or the lateral direction 32 of the absorbent article 10.

In an embodiment, the projections 90 and/or the land areas 116 can be provided such that the projections 90 are located in the crotch region 16 of the absorbent article 10, are located towards the perimeter of the absorbent article 10, and combinations thereof. In an embodiment, the projections 90 can have varying heights in different areas of the absorbent article 10. In such an embodiment, for example, the projections 90 can have a first height in an area of the absorbent article 10 and a different height in a different area of the absorbent article 10. In an embodiment, the projections 90 can have varying diameters in different areas of the absorbent article 10. In such an embodiment, for example, the projections 90 can have a first diameter in an area of the absorbent article 10 and can have a different diameter an another area of the absorbent article 10. In an embodiment, the concentration of projections 90 can vary in the absorbent article 10. In such an embodiment, an area of the absorbent article 10 can have a higher concentration of projections 90 than the concentration of projections 90 in a second area of the absorbent article 10.

In an embodiment, the projections 90 and/or the land areas 116 can be provided in a patterned orientation. Non-limiting examples of patterned orientations can include, but are not limited to, lines, circles, squares, rectangles, triangles, ovals, stars, and hexagons. In an embodiment, a patterned orientation can be provided such that the patterned orientation is parallel with the longitudinal direction 30 and/or the lateral direction 32 of the absorbent article 10. In an embodiment, a patterned orientation can be provided such that the patterned orientation is at an angle to the longitudinal direction 30 and/or the lateral direction 32 of the absorbent article 10. In an embodiment, a projection 90 of the body facing material 28 can be at least partially aligned, completely aligned, or completely non-aligned with another projection 90 of the body facing material 28, such as, for example, an adjacent projection 90. Without being bound by theory, it is believed that the alignment (whether partial, complete alignment or complete non-alignment) of a projection 90 of the body facing material 28 with another projection 90, such as an adjacent projection 90, of the body facing material 28 can result in channels of land areas 116 which can impede further spread of body exudates along the body facing material 28 of the absorbent article 10 and/or can direct the spread of body exudates towards desired locations of the body facing material 28 of the absorbent article 10.

The body facing material 28 can be the result of the movement of the fibers in the projection layer 94 in one and sometimes two or more directions. Referring to FIG. 9, if the forming surface upon which the projection layer 94 is placed is solid except for the forming holes used to form the projections 90, then the force of the fluid entangling streams hitting and rebounding off the solid surface land areas corresponding to the land areas 116 of the projection layer 94 can cause a migration of fibers adjacent the inner surface 102 of the projection layer 94 into the support layer 92 adjacent its second surface 98. This migration of fibers in the first direction can be represented by the arrows 126 shown in FIG. 9. In order to form the projections 90 extending outwardly from the outer surface 104 of the projection layer 94, there must be a migration of fibers in a second direction as shown by the arrows 128. It is this migration in the second direction which causes fibers from the projection layer 94 to move out and away from the outer surface 104 to form the projections 90.

In an embodiment in which the support layer 92 can be a fibrous nonwoven web, depending on the degree of web integrity and the strength and dwell time of the fluid jets, there also may be a movement of support layer 92 fibers into the projection layer 94 as shown by arrows 130 in FIG. 9. The net result of these fiber movements can be the creation of a body facing material 28 with good overall integrity and lamination of the layers (92 and 94) at their interface 108 thereby allowing further processing and handling of the body facing material 28. As a result of the fluid entanglement processes described herein, it is generally not desirable that the fluid pressure used to form the projections 90 be of sufficient force so as to force fibers from the support layer 92 to be exposed on the outer surface 104 of the projection layer 94.

Support Layer and Projection Layer of Body Facing Material

As the name implies, the support layer 92 can support the projection layer 94 containing the projections 90 and can be made from a number of structures provided the support layer 92 can be capable of supporting the projection layer 94. The primary functions of the support layer 92 can be to protect the projection layer 94 during the formation of the projections 90, to be able to bond to or be entangled with the projection layer 94 and to aid in further processing of the projection layer 94 and the resultant body facing material 28. Suitable materials for the support layer 92 can include, but are not limited to, nonwoven fabrics or webs, scrim materials, netting materials, paper/cellulose/wood pulp-based products which can be considered a subset of nonwoven fabrics or webs as well as foam materials, films and combinations of the foregoing provided the material or materials chosen are capable of withstanding a process of manufacture such as a fluid-entangling process. In an embodiment, the support layer 92 can be a fibrous nonwoven web made from a plurality of randomly deposited fibers which may be staple length fibers such as are used, for example, in carded webs, air laid webs, etc. or they may be more continuous fibers such as are found in, for example, meltblown or spunbond webs. Due to the functions the support layer 92 must perform, the support layer 92 can have a higher degree of integrity than the projection layer 94. In this regard, the support layer 92 can remain substantially intact when it is subjected to the fluid-entangling process. The degree of integrity of the support layer 92 can be such that the material forming the support layer 92 can resist being driven down into and filling the projections 90 of the projection layer 94. As a result, in an embodiment in which the support layer 92 is a fibrous nonwoven web, it should have a higher degree of fiber-to-fiber bonding and/or fiber entanglement than the fibers in the projection layer 94. While it can be desirable to have fibers from the support layer 92 entangle with the fibers of the projection layer 94 adjacent the interface 108 between the two layers, it is generally desired that the fibers of this support layer 92 not be integrated or entangled into the projection layer 94 to such a degree that large portions of these fibers find their way inside the projections 90.

In an embodiment, a function of the support layer 92 can be to facilitate further processing of the projection layer 94. In an embodiment, the fibers used to form the projection layer 94 can be more expensive than those used to form the support layer 92. As a result, in such an embodiment, it can be desirable to keep the basis weight of the projection layer 94 low. In so doing, however, it can become difficult to process the projection layer 94 subsequent to its formation. By attaching the projection layer 94 to an underlying support layer 92, further processing, winding and unwinding, storage and other activities can be done more effectively.

In order to resist the higher degree of fiber movement, as mentioned above, in an embodiment, the support layer 92 can have a higher degree of integrity than the projection layer 94. This higher degree of integrity can be brought about in a number of ways. One can be fiber-to-fiber bonding which can be achieved through thermal or ultrasonic bonding of the fibers to one another with or without the use of pressure as in through-air bonding, point bonding, powder bonding, chemical bonding, adhesive bonding, embossing, calender bonding, etc. In addition, other materials may be added to the fibrous mix such as adhesives and/or bicomponent fibers. Pre-entanglement of a fibrous nonwoven support layer 92 may also be used such as, for example, by subjecting the web to hydroentangling, needlepunching, etc., prior to this support layer 92 being joined to a projection layer 94. Combinations of the foregoing are also possible. Still other materials such as foams, scrims and nettings may have enough initial integrity so as to not need further processing. The level of integrity can in many cases be visually observed due to, for example, the observation with the unaided eye of such techniques as point bonding which is commonly used with fibrous nonwoven webs such as spunbond webs and staple fiber-containing webs. Further magnification of the support layer 92 may also reveal the use of fluid-entangling or the use of thermal and/or adhesive bonding to join the fibers together.

The type, basis weight, tensile strength and other properties of the support layer 92 can be chosen and varied depending upon the particular end use of the resultant body facing material 28. When the body facing material 28 is to be used as part of an absorbent article such as a personal care absorbent article, wipe, etc., it can be generally desirable that the support layer 92 be a layer that is fluid pervious, has good wet and dry strength, is able to absorb fluids such as body exudates, possibly retain the fluids for a certain period of time and then release the fluids to one or more subjacent layers. In this regard, fibrous nonwovens such as spunbond webs, meltblown webs and carded webs such as airlaid webs, bonded carded webs and coform materials are well-suited as support layers 92. Foam materials and scrim materials are also well-suited. In addition, the support layer 92 may be a multi-layered material due to the use of several layers or the use of multi-bank formation processes as are commonly used in making spunbond webs and meltblown webs as well as layered combinations of meltblown and spunbond webs. In the formation of such support layers 92, both natural and synthetic materials may be used alone or in combination to fabricate the materials. In various embodiments, the support layer 92 can have a basis weight ranging from about 5 to about 40 or 50 gsm.

The projection layer 94 can be made from a plurality of randomly deposited fibers which may be staple length fibers such as are used, for example, in carded webs, airlaid webs, coform webs, etc., or they may be more continuous fibers such as are found in, for example, meltblown or spunbond webs. The fibers in the projection layer 94 can have less fiber-to-fiber bonding and/or fiber entanglement and thus less integrity as compared to the integrity of the support layer 92, especially in embodiments when the support layer 92 is a fibrous nonwoven web. Alternatively, when both the support layer 92 and the projection layer 94 can both be fibrous nonwoven webs, the projection layer 94 can have less integrity than the support layer 92 due to the projection layer 94 having, for example, less fiber-to-fiber bonding, less adhesive or less pre-entanglement of the fibers forming the projection layer 94.

The projection layer 94 can have a sufficient amount of fiber movement capability to allow the below-described fluid entangling process to be able to move a first plurality of the plurality of fibers of the projection layer 94 out of the X-Y plane of the projection layer 94 and into the perpendicular or Z-direction of the projection layer 94 so as to be able to form the projections 90 (illustrated in FIG. 7). As noted herein, in various embodiments, the projections 90 can be hollow. As described herein, in an embodiment, a second plurality of the plurality of fibers in the projection layer 94 can become entangled with the support layer 92. If more continuous fiber structures are being used such as meltblown or spunbond webs, in an embodiment, there may be little or no pre-bonding of the projection layer 94 prior to the fluid entanglement process. Longer fibers such as are generated in meltblowing and spunbonding processes (which are often referred to as continuous fibers to differentiate them from staple length fibers) will typically require more force to displace the fibers in the Z-direction than will shorter, staple length fibers that typically have fiber lengths less than about 100 mm and more typically fibers lengths in the 10 to 60 mm range. Conversely, staple fiber webs such as carded webs and airlaid webs can have some degree of pre-bonding or entanglement of the fibers due to their shorter length. Such shorter fibers require less fluid force from the fluid entangling streams to move them in the Z-direction to form the projections 90. As a result, a balance must be met between fiber length, degree of pre-fiber bonding, fluid force, web speed and dwell time so as to be able to create the projections 90 without, unless desired, forming apertures in the land areas 116 or the projections 90 or forcing too much material into the interior space 124 of the projections 90 thereby making the projections 90 too rigid for some end-use applications. In addition to an interior space 124, the side walls 112 of the projection 90 have a thickness 122.

In various embodiments, the projection layer 94 can have a basis weight ranging from about 10 gsm to about 60 gsm. Spunbond webs can typically have basis weights of between about 15 and about 50 gsm when being used as the projection layer 94. Fiber diameters can range between about 5 and about 20 microns. The fibers may be single component fibers formed from a single polymer composition or they may be bicomponent or multicomponent fibers wherein one portion of the fiber can have a lower melting point than the other components so as to allow fiber-to-fiber bonding through the use of heat and/or pressure. Hollow fibers may also be used. The fibers may be formed from any polymer formulations typically used to form spunbond webs. Examples of such polymers include, but are not limited to, polypropylene ("PP"), polyester ("PET"), polyamide ("PA"), polyethylene ("PE") and polylactic acid ("PLA"). The spunbond webs may be subjected to post-formation bonding and entangling techniques if necessary to improve the processability of the web prior to its being subjected to the projection forming process.

Meltblown webs can typically have basis weights of between about 20 and about 50 gsm when being used as the projection layer 94. Fiber diameters can range between about 0.5 and about 5 microns. The fibers may be single component fibers formed from a single polymer composition or they may be bicomponent or multicomponent fibers wherein one portion of the fiber can have a lower melting point than the other components so as to allow fiber-to-fiber bonding through the use of heat and/or pressure. The fibers may be formed from any polymer formulations typically used to form spunbond webs. Examples of such polymers include, but are not limited to, PP, PET, PA, PE and PLA.

Carded and airlaid webs can use staple fibers that can typically range in length between about 10 and about 100 millimeters. Fiber denier can range between about 0.5 and about 6 denier depending upon the particular end use. Basis weights can range between about 20 and about 60 gsm. The staple fibers may be made from a wide variety of polymers including, but not limited to, PP, PET, PA, PE, PLA, cotton, rayon, flax, wool, hemp and regenerated cellulose such as, for example, Viscose. Blends of fibers may be utilized too, such as blends of bicomponent fibers and single component fibers as well as blends of solid fibers and hollow fibers. If bonding is desired, it may be accomplished in a number of ways including, for example, through-air bonding, calender bonding, point bonding, chemical bonding and adhesive bonding such as powder bonding. If needed, to further enhance the integrity and processability of a projection layer 94 prior to the projection forming process, the projection layer 94 may be subjected to pre-entanglement processes to increase fiber entanglement within the projection layer 94 prior to the formation of the projections 90. Hydroentangling can be advantageous in this regard.

While the foregoing nonwoven web types and formation processes described herein are suitable for use in conjunction with the projection layer 94, it is anticipated that other webs and formation processes may also be used provided the webs are capable of forming the projections 90.

The support layer 92 and the projection layer 94 each can be made at a variety of basis weights depending upon the particular end application. For example, the body facing material 28 can have an overall basis weight from about 15, 20 or 25 to about 100, 110 or 120 gsm and the support layer 92 can have a basis weight from about 5 to about 40 or 50 gsm while the projection layer 94 can have a basis weight from about 15 or 20 to about 50 or 60 gsm. Such basis weight ranges can be possible due to the manner in which the body facing material 28 can be formed and the use of two different layers with different functions relative to the formation process. As a result, the body facing material 28 can be made in commercial settings which heretofore were not considered possible due to the inability to process the individual webs and form the desired projections 90. The body facing material 28 described herein is consistent with the material described in U.S. Pat. No. 9,474,660 issued to Kirby et al., which is incorporated herein by reference.

Secondary Liner:

In various embodiments, the body facing material 28 of the absorbent article 10 can overlay the absorbent body 40 and the outer cover 26 and can isolate the wearer's skin from liquid waste retained by the absorbent body 40. In various embodiments, the body facing material 28 can overlay a secondary liner 34. In such embodiments, the secondary liner 34 can overlay the absorbent body 40. In various embodiments, a fluid transfer layer 78 can be positioned between the secondary liner 34 and the absorbent body 40. In various embodiments, an acquisition layer 84 can be positioned between the secondary liner 34 and the absorbent body 40 or a fluid transfer layer 78, if present. In various embodiments, the secondary liner 34 can be bonded to the acquisition layer 84, or the fluid transfer layer 78 if no acquisition layer 84 is present, via adhesive and/or by a point fusion bonding. The point fusion bonding may be selected from ultrasonic, thermal, pressure bonding, and combinations thereof.

In an embodiment, the secondary liner 34 can extend beyond the absorbent body 40 and/or a fluid transfer layer 78, and/or an acquisition layer 84 to overlay a portion of the outer cover 26 and can be bonded thereto by any method deemed suitable, such as, for example, by being bonded thereto by adhesive, to substantially enclose the absorbent body 40 between the outer cover 26 and the secondary liner 34. The secondary liner 34 may be narrower than the outer cover 26, but it is to be understood that the secondary liner 34 and the outer cover 26 may be of the same dimensions.

It is also contemplated that the secondary liner 34 may not extend beyond the absorbent body 40 and/or may not be secured to the outer cover 26. The secondary liner 34 can be suitably compliant, soft feeling, and non-irritating to the wearer's skin and can be the same as or less hydrophilic than the absorbent body 40 to permit body exudates to readily penetrate through to the absorbent body 40 and provide a relatively dry surface to the wearer.

The secondary liner 34 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the secondary liner 34. The secondary liner 34 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof.

For example, the secondary liner 34 can be composed of a meltblown or spunbond web of polyolefin fibers. Alternatively, the secondary liner 34 can be a bonded-carded web composed of natural and/or synthetic fibers. The secondary liner 34 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire secondary liner 34 or it can be selectively applied to particular sections of the secondary liner 34. In an embodiment, the secondary liner 34 can be treated with a modifier which can increase the surface energy of the material surface or reduce the viscoelastic properties of body exudates, such as menses.

In an embodiment, a secondary liner 34 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a secondary liner 34 can be a spunbond substrate with a basis weight from about 10 or 12 to about 15 or 20 gsm. In an embodiment, a secondary liner 34 can be a 12 gsm spunbond-meltblown-spunbond substrate having 10% meltblown content applied between the two spunbond layers.

Although the outer cover 26 and secondary liner 34 can include elastomeric materials, it is contemplated that the outer cover 26 and the secondary liner 34 can be composed of materials which are generally non-elastomeric. In an embodiment, the secondary liner 34 can be stretchable, and more suitably elastic. In an embodiment, the secondary liner 34 can be suitably stretchable and more suitably elastic in at least the lateral or circumferential direction of the absorbent article 10. In other aspects, the secondary liner 34 can be stretchable, and more suitably elastic, in both the lateral and the longitudinal directions.

Containment Flaps:

In an embodiment, containment flaps, 50 and 52, can be secured to the body facing material 28 and/or, if present, the secondary liner 34, of the absorbent article 10 in a generally parallel, spaced relation with each other laterally inward of the leg openings 56 to provide a barrier against the flow of body exudates to the leg openings 56. In an embodiment, the containment flaps, 50 and 52, can extend longitudinally from the front waist region 12 of the absorbent article 10, through the crotch region 16 to the back waist region 14 of the absorbent article 10. The containment flaps, 50 and 52, can be bonded to the body facing material 28 and/or the secondary liner 34 by a seam of adhesive 137 to define a fixed proximal end 138 of the containment flaps, 50 and 52.

The containment flaps, 50 and 52, can be constructed of a fibrous material which can be similar to the material forming the body facing material 28 and/or the secondary liner 34, if present. Other conventional material, such as polymer films, can also be employed. Each containment flap, 50 and 52, can have a moveable distal end 136 which can include flap elastics, such as flap elastics 58 and 60, respectively. Suitable elastic materials for the flap elastic, 58 and 60, can include sheets, strands or ribbons of natural rubber, synthetic rubber, or thermoplastic elastomeric materials.

The flap elastics, 58 and 60, as illustrated, can have two strands of elastomeric material extending longitudinally along the distal ends 136 of the containment flaps, 50 and 52, in generally parallel, spaced relation with each other. The elastic strands can be within the containment flaps, 50 and 52, while in an elastically contractible condition such that contraction of the strands gathers and shortens the distal ends 136 of the containment flaps, 50 and 52. As a result, the elastic strands can bias the distal ends 136 of each containment flap, 50 and 52, toward a position spaced from the proximal end 138 of the containment flaps, 50 and 52, so that the containment flaps, 50 and 52, can extend away from the body facing material 28 and/or the secondary liner 34 in a generally upright orientation of the containment flaps, 50 and 52, especially in the crotch region 16 of the absorbent article 10, when the absorbent article 10 is fitted on the wearer. The distal end 136 of the containment flaps, 50 and 52, can be connected to the flap elastics, 58 and 60, by partially doubling the containment flap, 50 and 52, material back upon itself by an amount which can be sufficient to enclose the flap elastics, 58 and 60. It is to be understood, however, that the containment flaps, 50 and 52, can have any number of strands of elastomeric material and may also be omitted from the absorbent article 10 without departing from the scope of this disclosure.

Leg Elastics:

Leg elastic members, 66 and 68, can be secured between the outer and inner layers, 70 and 72, respectively, of the outer cover 26, such as by being bonded therebetween by laminate adhesive, generally adjacent the lateral outer edges of the inner layer 72 of the outer cover 26. Alternatively, the leg elastic members, 66 and 68, may be disposed between other layers of the absorbent article 10. A wide variety of elastic materials may be used for the leg elastic members, 66 and 68. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate.

Fastening System:

In an embodiment, the absorbent article 10 can include a fastener system. The fastener system can include one or more back fasteners 140 and one or more front fasteners 142. Portions of the fastener system may be included in the front waist region 12, back waist region 14, or both. The fastener system can be configured to secure the absorbent article 10 about the waist of the wearer and maintain the absorbent article 10 in place during use. In an embodiment, the back fasteners 140 can include one or more materials bonded together to form a composite ear as is known in the art. For example, the composite fastener may be composed of a stretch component 144, a nonwoven carrier or hook base 146, and a fastening component 148.

Waist Elastic Members:

In an embodiment, the absorbent article 10 can have waist elastic members, 62 and 64, which can be formed of any suitable elastic material. In such an embodiment, suitable elastic materials can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist elastic members, 62 and 64, may be omitted from the absorbent article 10 without departing from the scope of this disclosure.

Attachment of Body Facing Material to Underlying Elements:

The body facing material 28 of the invention may be attached to one or more of the components of the absorbent article 10 underneath it including the absorbent body 40, the secondary liner 34, the fluid transfer layer 78 or the acquisition layer 84. As described herein, the body facing material 28 may include apertures 120 formed through both the support layer 92 and the projection layer 94. Together, the apertures 120 form an aperture area 150. Within the body facing material 28, the apertures 120 are surrounded by land area 116. With attachment of the body facing material 28 to one or more of the other components, it is desirable that the apertures 120 not be covered or occluded by the attachment material. The body facing material 28 may be attached or bonded, for example, to the secondary liner 34 by one or more means typically known for constructing absorbent articles 10 including, but not limited to, adhesive bonding and mechanical bonding. The mechanical bonding may be formed by point fusion bonds selected from pressure bonds, thermal bonds, ultrasonic bonds and combinations thereof. If the apertures 120 are covered by the adhesive or mechanical bonds, the function of the apertures 120 related to absorbing exudates is compromised. While the mechanical bonds may compromise the purpose of the apertures 120, combination of the apertures 120 with adhesive is more disadvantageous because the adhesive may stick to the skin of the wearer of the absorbent article 10. A purpose of the apertures 120 is to provide a channel through which the exudates may pass to be drawn within the absorbent article 10, but if the apertures 120 are covered or blocked, the exudates cannot pass through. In an aspect of the present invention, the body facing material 28 includes an aperture area 150 and is bonded to a secondary liner 34; the attachment between the body facing material 28 and the secondary liner 34 is achieved by a bonded area 160 that is separate and discrete from the aperture area 150.

FIG. 10A depicts an illustrative embodiment of a body facing material 28 including an aperture area 150 and a bonded area 160. The body facing material 28 includes a width 152 in the lateral direction 32 and a length 154 in the longitudinal direction 30. The body facing material 28 of FIG. 10A further includes opposed first and second lateral edges 156, that extend along the length 154 in the longitudinal direction 30. The body facing material 28 also includes a front edge 158 and a back edge 159, that extend along the length 152 in the lateral direction 32. With the body facing material 28 depicted in FIG. 10A, the aperture area 150 extends the full length 154 of the body facing material 28. The length of the aperture area 150 may be the same as the length 154 of the body facing material 28 or it may be less than the length 154 of the body facing material 28. Additionally, the width of the aperture area 150 may be the same as the width 152 of the body facing material or it may be less than the width 152 of the body facing material 28. The body facing material 28 has four bonded areas 160, two on each of the lateral edges 156 of the body facing material 28 that extend along at least a portion of the lateral edges 156, but do not extend the full length 154 of the body facing material 28. The bonded areas 160 shown in FIG. 10A may be formed by an adhesive that is located between the body facing material 28 and a secondary liner 34.

The width of the aperture area 150 may be selected to be 10% to 90% of the width 152 of the body facing material 28. The bonded area 160 may begin at the lateral edge 156 of the body facing material 28 and extend inward in the lateral direction 32. The bonded area 160 may end before the beginning of the aperture area 150, or it may end next to the beginning of the aperture area 150. When the bonded area 160 is formed by adhesive, the adhesive may be applied by a non-contact spray nozzle, contact bead application or slot coat wipe. The width of the bonded area 160 may be selected based on the overall width of the body facing material 28 and the width of the aperture area 150. The bonded area 160 may begin at the lateral edge 156 of the body facing material or it may begin 3 mm inward from the lateral edge. The width of the bonded area 160 may be selected based on the overall configuration of the body facing material 28. For example, when using a spray nozzle applicator, the bonded area 160 may be formed of a constructive adhesive (as are well known in the art) and have a width of 12 mm. Spray nozzle applicators capable of forming the bonded area 160 of this design are "half width" Nordson Summit nozzles (standard pattern, 25 mm).

With regard to the apertures 120, the spacing between apertures 120 may be selected based on the location and/or pattern of the aperture area 150 desired in the body facing material 28. The spacing between apertures 120 may be selected based on the desired registration with the projections 90. In one aspect, the spacing of the apertures 120 on a center-to-center basis may be between 3 mm and 100 mm. In another aspect, the spacing of the apertures 120 may be between 5 mm and 30 mm on a center-to-center basis. In a further aspect, the pattern of spacing between apertures 120 may be non-uniform such that there is a higher density of apertures 120 in one area/location of the body facing material 28 than in a neighboring area/location. In a representative aspect, the apertures 120 are arranged in "array lanes"; an "array lane" is a pattern of apertures 120 that may extend across the width 152 of the body facing material 28. A group of array lanes may be located in proximity to each other to form a bigger pattern of apertures 120; the pattern of apertures 120 forms the aperture area 150.

FIG. 10B depicts a representative embodiment of the body facing material 28 of the invention that includes an aperture area 150 and two bonded areas 160. The aperture area 150 extends the full length 154 of the body facing material 28. The two bonded areas 160 extend the full length 154 of the body facing material 28 and are located proximate the lateral edges 156 of the body facing material 28.

FIG. 10C also depicts a representative embodiment of the body facing material 28 in which there are two aperture areas 150 that are separated by a land area. Both of the aperture areas 150 extend the full length 154 of the body facing material 28. The body facing material 28 also includes two bonded areas 160 that are located near the lateral edges 156 of the body facing material 28 and that extend the full length 154 of the body facing material 28. There is an additional bonded area 162 that is located on the land area between the two aperture areas 150 and the additional bonded area 162 extends the full length 154 of the body facing material 28. FIG. 10D depicts a representative embodiment of the body facing material 28 that is similar to FIG. 10C, except the embodiment of FIG. 10D includes three aperture areas 150 that are separated by two land areas. All three aperture areas 150 extend the full length 154 of the body facing material 28. The embodiment of FIG. 10D includes two additional bonded areas 162 that are located on the land areas between the three aperture areas 150. Both additional bonded areas 162 extend the full length 154 of the body facing material 28. FIG. 10E depicts a representative embodiment of the body facing material 28 that is similar to FIG. 10D except that there are four additional bonded areas 162 that are located on the land areas between the three aperture areas; the four additional bonded areas 162, however, do not extend the full length 154 of the body facing material 28.

Figure 10F:
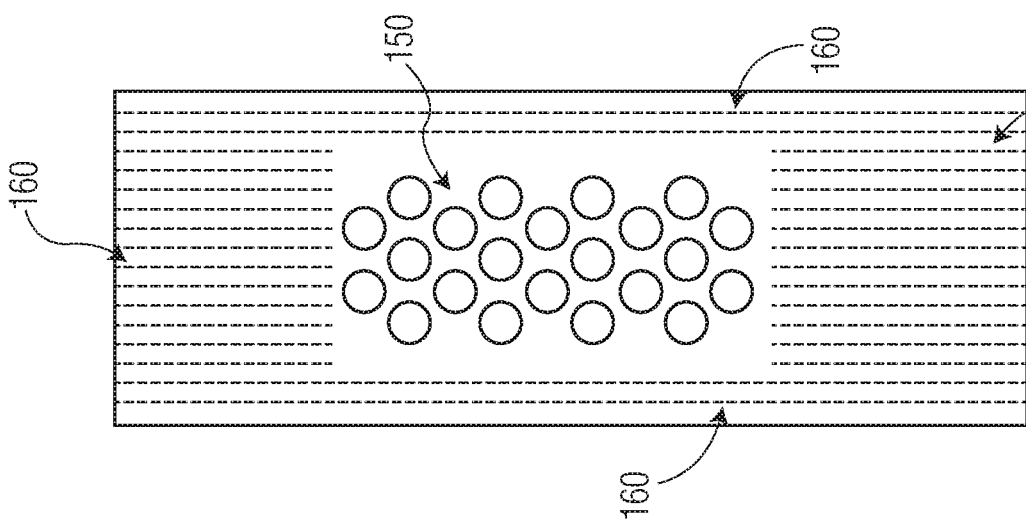
FIG. 10F is a top down view of an illustrative embodiment of a body facing material in which there is an aperture area that forms a "window" near the center of the body facing material. The bonded area surrounds the "window" of the aperture area.
Figure 10E:
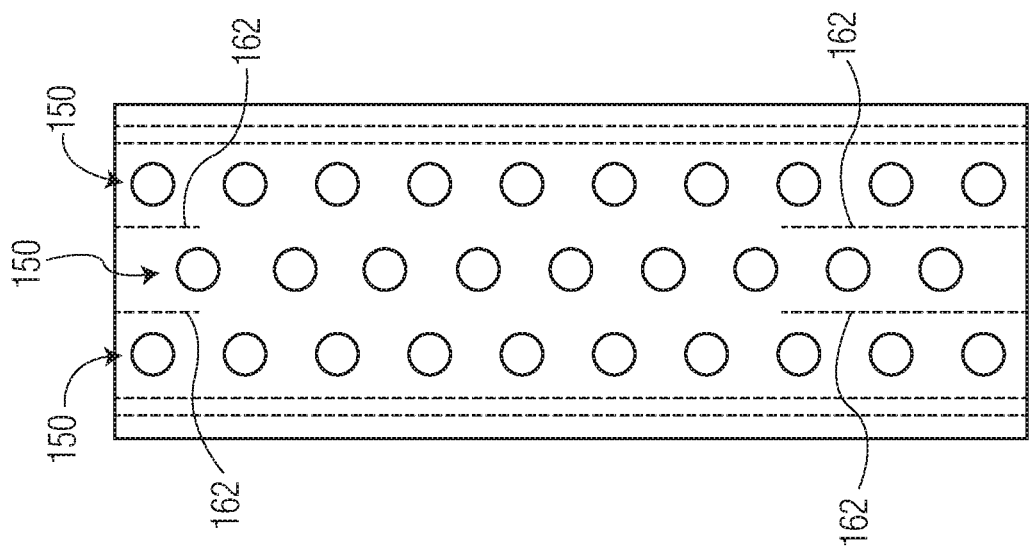
FIG. 10E is similar to FIG. 10D except the bonded areas located between the aperture areas do not extend the full length of the body facing material.
Figure 10D:
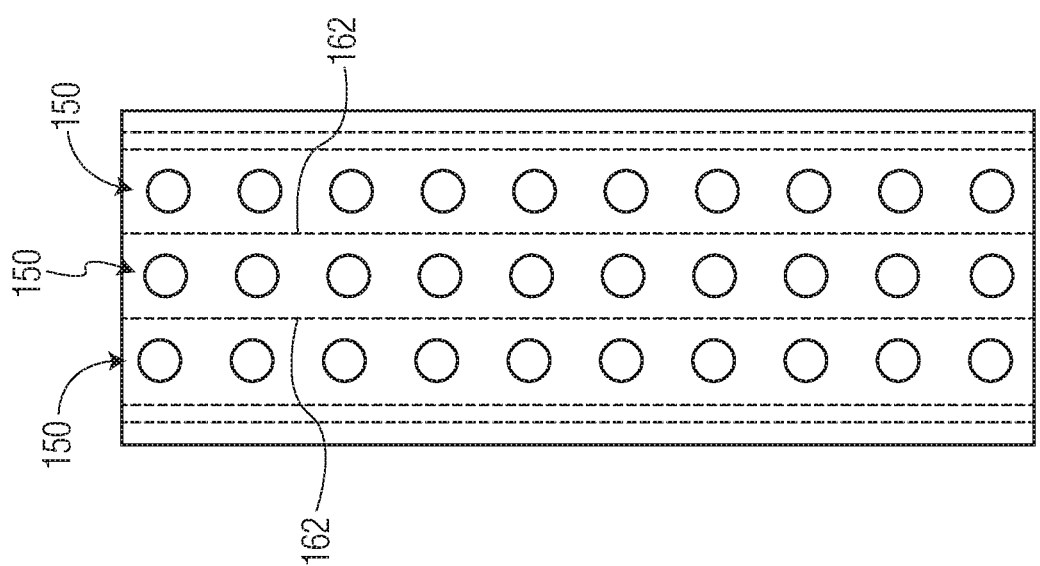
FIG. 10D is similar to FIG. 10C except that there are three aperture areas and two bonded areas on the land areas between the aperture areas.

FIG. 10F depicts a representative embodiment of the body facing material 28 of the invention in which the aperture area 150 forms a "window" proximate the center area of the body facing material 28. The bonded area 160 surrounds, but does not touch the aperture area 150. With this embodiment, the bonded area 160 begins along the full length 154 of the lateral edges 156 of the body facing material 28. The bonded area 160 extends inward in the lateral direction 32 toward the center of the body facing material 28 until the aperture area 150 begins. Similarly, the bonded area 160 extends from the front edge 158 and the back edge 159 of the body facing material 28 inward in longitudinal direction 30 toward the center of the body facing material until the aperture area 150 begins. A benefit of having a bonded area 160 to attach the body facing material 28 to a secondary liner 34 is to hold the body facing material 28 in place so that the it does not adhere or otherwise stick to the skin of the wearer of the absorbent article.

In another aspect, the present invention is also directed to absorbent articles 10 having a fluid-entangled body facing material 28 that is attached to a secondary liner 34 by an adhesive bonded area 170 and a mechanical bonded area 180. The mechanical bonded area 180 may be formed by one or more point fusion bonds. The point fusion bonds may be selected from ultrasonic, thermal, pressure bonding, and combinations thereof. The fluid-entangled body facing material 28 includes a plurality of hollow projections and a plurality of apertures, wherein the plurality of apertures define an aperture area 150. The aperture area 150 is discrete from the adhesive bonded area 170. The body facing material 28 includes a width 152 in the lateral direction 32 and a length 154 in the longitudinal direction 30. The body facing material 28 also includes opposed first and second lateral edges 156 that extend the length 154 of the body facing material 28. Additionally, the body facing material 28 includes a front edge 158 and a back edge 159, where both of these edges extend the length 152 of the body facing material 28 in the lateral direction 32. With this aspect of the invention, the adhesive bonded area 170—that provides part of the attachment of the body facing material 28 to the secondary liner 34—extends along at least a portion of the first and the second lateral edges 156. The aperture area 150 of the body facing material 28 has a length in the longitudinal direction 30 and a width in the lateral direction 32; the width of the aperture area 150 may be less than the width 152 of the body facing material 28. The length of the aperture area 150 may be the same (equal to) the length 154 of the body facing material 28, or, alternatively, the length of the aperture area 150 may be less than the length 154 of the body facing material 28. The adhesive bonded area 170 is discrete from the aperture area 150 in order to prevent adhesive becoming exposed through the apertures 120 and potentially coming into contact with the skin of the wearer of the absorbent article 10 in use and in order to maintain the function of the apertures 120 to receive exudates in order to help separate them from the wearer's skin.

FIG. 11A depicts a representative embodiment of a body facing material 28 of the invention in which the aperture area 150 extends the length 154 of the body facing material 28. The body facing material 28 includes adhesive bonded areas 170 that extend along the full length 154 of the first and second lateral edges 156. These adhesive bonded areas 170 are discrete from the aperture area 150. The embodiment of FIG. 11A also includes mechanical bonded areas 180 that extend along the front edge 158 and along the back edge 159 of the body facing material 28. Said differently, the mechanical bonded areas 180 extend from the first lateral edge 156 to the second lateral edge 156 of the body facing material 28; one of the mechanical bonded areas 180 is at the front edge 158 and one is at the back edge 159 of the body facing material 28.

FIG. 11B is similar to FIG. 11A in that it includes all of the features of the representative embodiment of FIG. 11A. In addition, the representative embodiment of FIG. 11B includes additional mechanical bonded areas 180. The additional mechanical bonded areas 180 also extend from the first lateral edge 156 to the second lateral edge 156. The additional mechanical bonded areas 180 are located between the mechanical bonded area 180 at the front edge 158 of the body facing material 28 and the mechanical bonded area 180 at the back edge 159 of the body facing material 28. While the mechanical bonded areas 180 are located over portions of the aperture area 150, they do not substantially interfere with the desired function and performance of the aperture area 150 and the mechanical bonded areas 180 do not affect the skin of the wearer of the absorbent article 10.

Figure 11D:
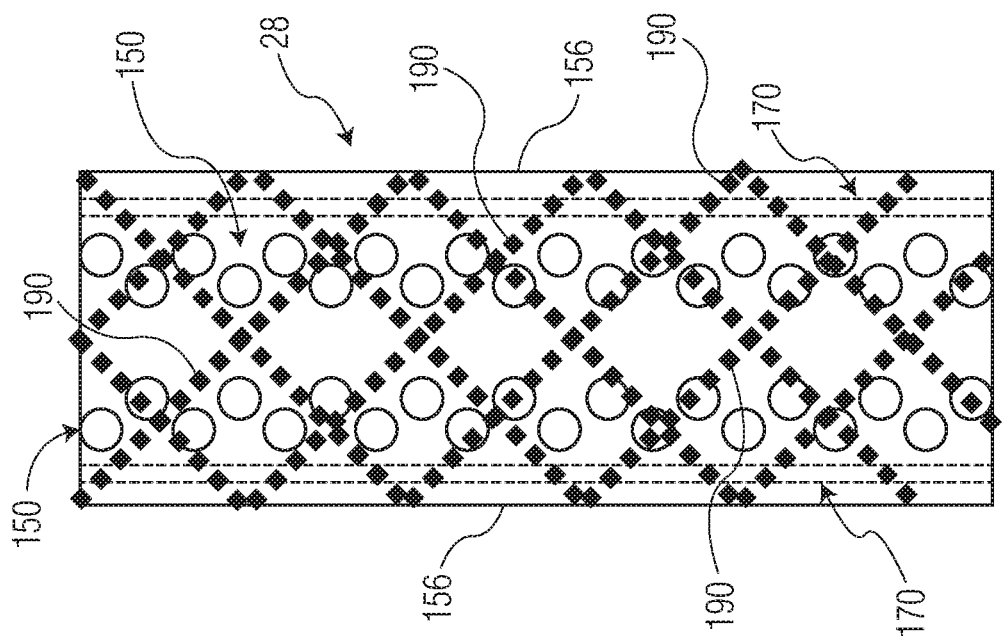
FIG. 11D is a top down view of an illustrative embodiment of a body facing material in which there are two aperture areas extending the full length of the body facing material and in which there is an adhesive bonded area on both lateral edges of the body facing material where the adhesive bonded area extends the full length of the body facing material. The body facing material also includes lines of mechanical bonds where each line begins at the first lateral edge and ends at the second lateral edge.
Figure 11C:
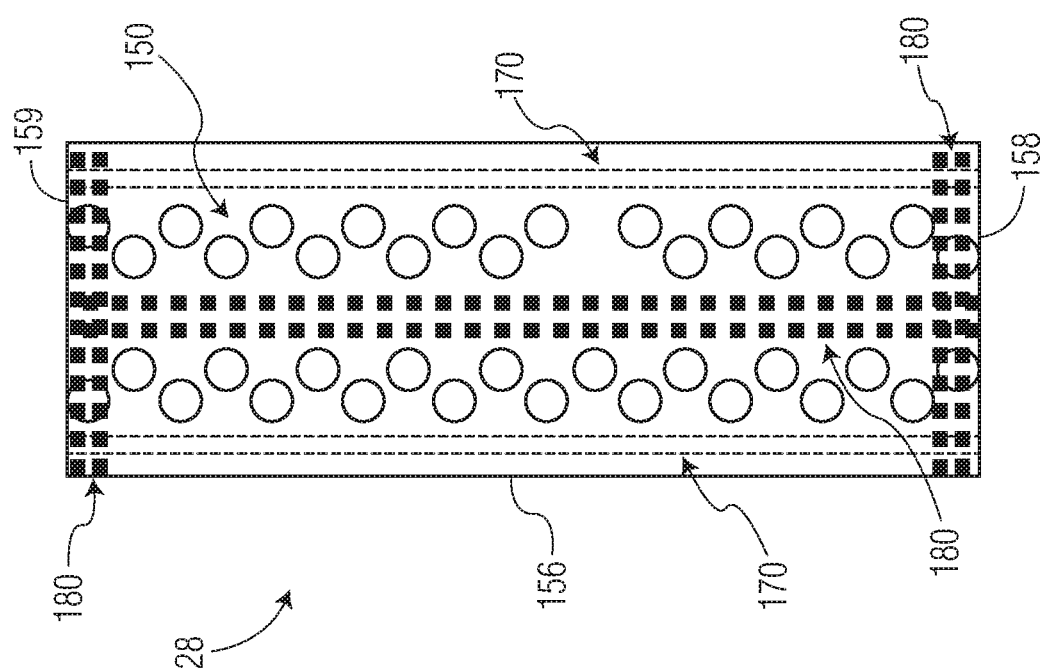
FIG. 11C is similar to FIG. 10A except that there is an additional mechanical bonded area that extends from the front edge to the back edge along a centerline of the body facing material.

FIG. 11C is similar to FIG. 11A except that there are two aperture areas 150 with a land area separating them. In addition to the mechanical bonded areas 180 located at the front edge 158 and the back edge 159 of the body facing material 28, there is an additional mechanical bonded area 180 that extends the full length 154 of the body facing material through the land area separating the two aperture areas 150. Therefore, the third mechanical bonded area 180 extends from the front edge 158 to the back edge 159 of the body facing material. With the representative embodiment shown in FIG. 11C, the third mechanical bonded area 180 is positioned approximately along a longitudinal centerline of the body facing material 28.

FIG. 11D depicts another representative embodiment of a body facing material 28 of the invention. With this embodiment, there are two aperture areas 150 extending the full length 154 of the body facing material 28 with a land area in between them. The embodiment has adhesive bonded areas 170 along both lateral edges 156 where the adhesive bonded areas 170 extend the full length 154 of the body facing material 28. The body facing material 28 also includes lines of mechanical bonds 190 where each line 190 begins at the first lateral edge 156 and ends at the second lateral edge 156, forming a criss-cross pattern. Each line of mechanical bonds 190, individually or collectively, forms the mechanical bonded area 180. The individual bonds of the lines 190 may be point fusion bonds that are selected from ultrasonic, thermal, pressure bonding, and combinations thereof.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article including a longitudinal direction and a lateral direction and having a front waist region, a back waist region and a crotch region between the front waist region and the back waist region, the absorbent article comprising:
   a) a fluid-entangled body facing material comprising:
      i) a support layer comprising a plurality of fibers and opposed first and second surfaces;
      ii) a projection layer comprising a plurality of fibers and opposed inner and outer surfaces, the second surface of the support layer in contact with the inner surface of the projection layer, fibers of at least one of the support layer and the projection layer being fluid-entangled with fibers of the other of the support layer and the projection layer;

iii) a plurality of hollow projections formed from a first plurality of the plurality of fibers in the projection layer, the plurality of hollow projections extending from the outer surface of the projection layer in a direction away from the support layer;

iv) a plurality of apertures formed through the support layer and the projection layer, wherein the plurality of apertures define an aperture area on the body facing material; and v) a land area, wherein the plurality of hollow projections and the plurality of apertures are surrounded by the land area;

b) an outer cover; and c) an absorbent body positioned between the body facing material and the outer cover, the absorbent body having a width in the lateral direction and a length in the longitudinal direction; and d) a secondary liner including a width in the lateral direction and a length in the longitudinal direction, the width of the secondary liner being greater than the width of the absorbent body and the length of the secondary liner being greater than the length of the absorbent body, wherein the body facing material is attached to the secondary liner by a mechanical bonded area that extends through at least a portion of the aperture area.

2. The absorbent article of claim 1 wherein the body facing material includes a width in the lateral direction and a length in the longitudinal direction; the body facing material further includes opposed first and second lateral edges extending along the length in the longitudinal direction and includes a front edge and a back edge, both extending along the length in the lateral direction, wherein the mechanical bonded area extends along at least a portion of the first and second lateral edges.

3. The absorbent article of claim 2 wherein the aperture area has a length in the longitudinal direction and a width in the lateral direction; wherein the width of the aperture area is less than the width of the body facing material; and wherein the length of the aperture area is equal to the length of the body facing material.

4. The absorbent article of claim 2 wherein the aperture area has a length in the longitudinal direction and a width in the lateral direction; wherein the width of the aperture area is less than the width of the body facing material; and wherein the length of the aperture area is less than the length of the body facing material.

5. The absorbent article of claim 3, wherein the mechanical bonded area extends from the first and second lateral edges of the body facing material in the lateral direction and through the aperture area.

6. The absorbent article of claim 3, wherein the body facing material further includes a second aperture area separated from the aperture area by a land area and wherein the land area separating the aperture area from the second aperture area is attached to the secondary liner.

7. The absorbent article of claim 4, wherein the mechanical bonded area extends from the first and second lateral edges of the body facing material in the lateral direction; extends from the front and back edges of the body facing material in the longitudinal direction; and extends through the aperture area.

8. The absorbent article of claim 1, wherein the mechanical bonded area that attaches the body facing material to the secondary liner is formed with a plurality of discrete mechanical bonds.

9. An absorbent article including a longitudinal direction and a lateral direction and having a front waist region, a back waist region and a crotch region between the front waist region and the back waist region, the absorbent article comprising:

a) a fluid-entangled body facing material comprising:

i) a support layer comprising a plurality of fibers and opposed first and second surfaces;

ii) a projection layer comprising a plurality of fibers and opposed inner and outer surfaces, the second surface of the support layer in contact with the inner surface of the projection layer, fibers of at least one of the support layer and the projection layer being fluid-entangled with fibers of the other of the support layer and the projection layer;

iii) a plurality of hollow projections formed from a first plurality of the plurality of fibers in the projection layer, the plurality of hollow projections extending from the outer surface of the projection layer in a direction away from the support layer;

iv) a plurality of apertures formed through the support layer and the projection layer, wherein the plurality of apertures define an aperture area on the body facing material; and v) a land area, wherein the plurality of hollow projections and the plurality of apertures are surrounded by the land area;

b) an outer cover; and c) an absorbent body positioned between the body facing material and the outer cover, the absorbent body having a width in the lateral direction and a length in the longitudinal direction; and d) a secondary liner including a width in the lateral direction and a length in the longitudinal direction, the width of the secondary liner being greater than the width of the absorbent body and the length of the secondary liner being greater than the length of the absorbent body, wherein the body facing material is attached to the secondary liner by an adhesive bonded area that is discrete from the aperture area and by a mechanical bonded area, the mechanical bonded area extending through at least a portion of the aperture area.

10. The absorbent article of claim 9 wherein the body facing material includes a width in the lateral direction and a length in the longitudinal direction; the body facing material further includes opposed first and second lateral edges extending along the length in the longitudinal direction and includes a front edge and a back edge, both extending along the length in the lateral direction, wherein the adhesive bonded area extends along at least a portion of the first and second lateral edges.

11. The absorbent article of claim 10 wherein the aperture area has a length in the longitudinal direction and a width in the lateral direction; wherein the width of the aperture area is less than the width of the body facing material; and wherein the length of the aperture area is equal to the length of the body facing material.

12. The absorbent article of claim 10 wherein the aperture area has a length in the longitudinal direction and a width in the lateral direction; wherein the width of the aperture area is less than the width of the body facing material; and wherein the length of the aperture area is less than the length of the body facing material.

13. The absorbent article of claim 11, wherein the mechanical bonded area extends from the first lateral edge of the body facing material to the second lateral edge at the front edge of the body facing material.

14. The absorbent article of claim 13 further including a second mechanical bonded area that extends from the first lateral edge of the body facing material to the second lateral edge at the back edge of the body facing material.

15. The absorbent article of claim 14 further including additional mechanical bonded areas located between the mechanical bonded area at the front edge of the body facing material and the back edge of the body facing material.

16. The absorbent article of claim 9 wherein the mechanical bonded area is formed of pressure bonds formed by pressure bonding or ultrasonic bonds formed by ultrasonic bonding.

17. The absorbent article of claim 11 wherein the mechanical bonded area is formed by at least one line of mechanical bonds, wherein the line begins on the first lateral edge of the body facing material and ends on the second lateral edge.

18. The absorbent article of claim 14 further including an additional bonded area that extends from the front edge of the body facing material to the back edge of the body facing material, extending the length in the longitudinal direction of the body facing material.

19. The absorbent article of claim 8, wherein at least some of the plurality of discrete mechanical bonds are disposed through apertures of the apertured area.

20. The absorbent article of claim 9, wherein the mechanical bonded area comprises a plurality of discrete mechanical bonds and wherein at least some of the plurality of discrete mechanical bonds are disposed through apertures of the apertured area.

* * * * *